United States Patent [19]

Kuramoto et al.

[11] Patent Number: 5,395,030
[45] Date of Patent: Mar. 7, 1995

[54] SURGICAL DEVICE FOR STAPLING AND FASTENING BODY TISSUES

[75] Inventors: Seiji Kuramoto; Shiro Bito; Minoru Tsuruta; Shuichi Kimura; Akito Mukaizawa; Tsuyoshi Tsukagoshi; Akihiro Taguchi; Akio Nakada, all of Tokyo, Japan

[73] Assignee: Olympus Optical Co., Ltd., Tokyo, Japan

[21] Appl. No.: 70,736

[22] Filed: Jun. 2, 1993

[30] Foreign Application Priority Data

Jun. 4, 1992 [JP] Japan .................... 4-144464
Mar. 22, 1993 [JP] Japan .................... 5-085185

[51] Int. Cl.⁶ .......................................... A61B 17/068
[52] U.S. Cl. ..................................... 227/179; 227/19; 128/4
[58] Field of Search ................... 227/179, 180, 19; 128/4, 6, 305; 606/14

[56] References Cited

U.S. PATENT DOCUMENTS

| 3,954,108 | 5/1976 | Davis . | |
|---|---|---|---|
| 4,402,311 | 9/1983 | Hattori | 128/4 |
| 4,732,156 | 3/1988 | Nakamura | 128/4 |
| 4,928,699 | 5/1990 | Sasai | 128/4 |
| 4,955,882 | 9/1990 | Hakky | 606/14 |
| 5,005,749 | 4/1991 | Aranyi . | |
| 5,040,715 | 8/1991 | Green et al. . | |
| 5,084,057 | 1/1992 | Green et al. . | |
| 5,100,420 | 3/1992 | Green et al. . | |
| 5,197,649 | 3/1993 | Bessler et al. | 128/4 |

FOREIGN PATENT DOCUMENTS 59-501777 10/1984 Japan .
63-305854 12/1988 Japan .

*Primary Examiner*—Scott A. Smith
*Attorney, Agent, or Firm*—Frishauf, Holtz, Goodman & Woodward

[57] ABSTRACT

A surgical device for stapling and fastening body tissues, which comprises a staple-applying section containing a plurality of staples, a staple pusher incorporated in the staple-applying section, for applying the staples, an anvil section for deforming the staples, thereby to staple the body tissues together, an operation section for operating the staple pusher and the anvil section, an observation window located near the anvil section, and an ocular section for displaying images supplied from the observation window.

7 Claims, 31 Drawing Sheets

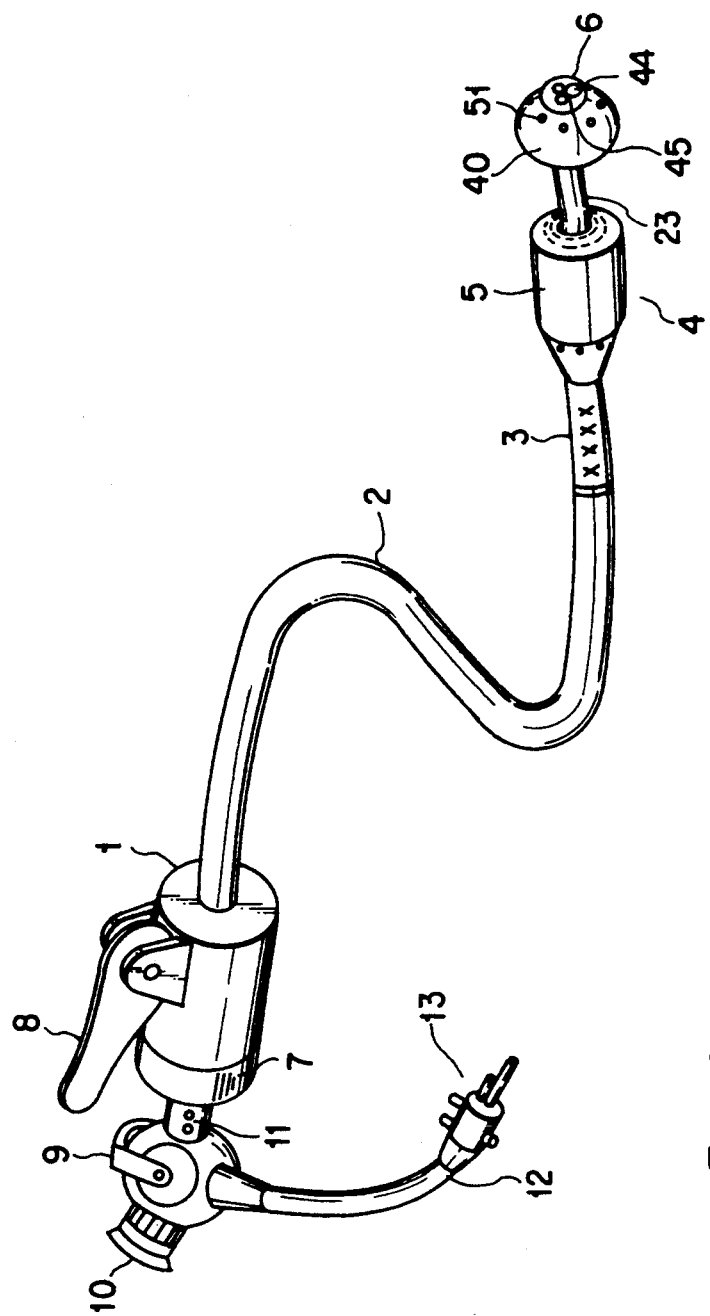

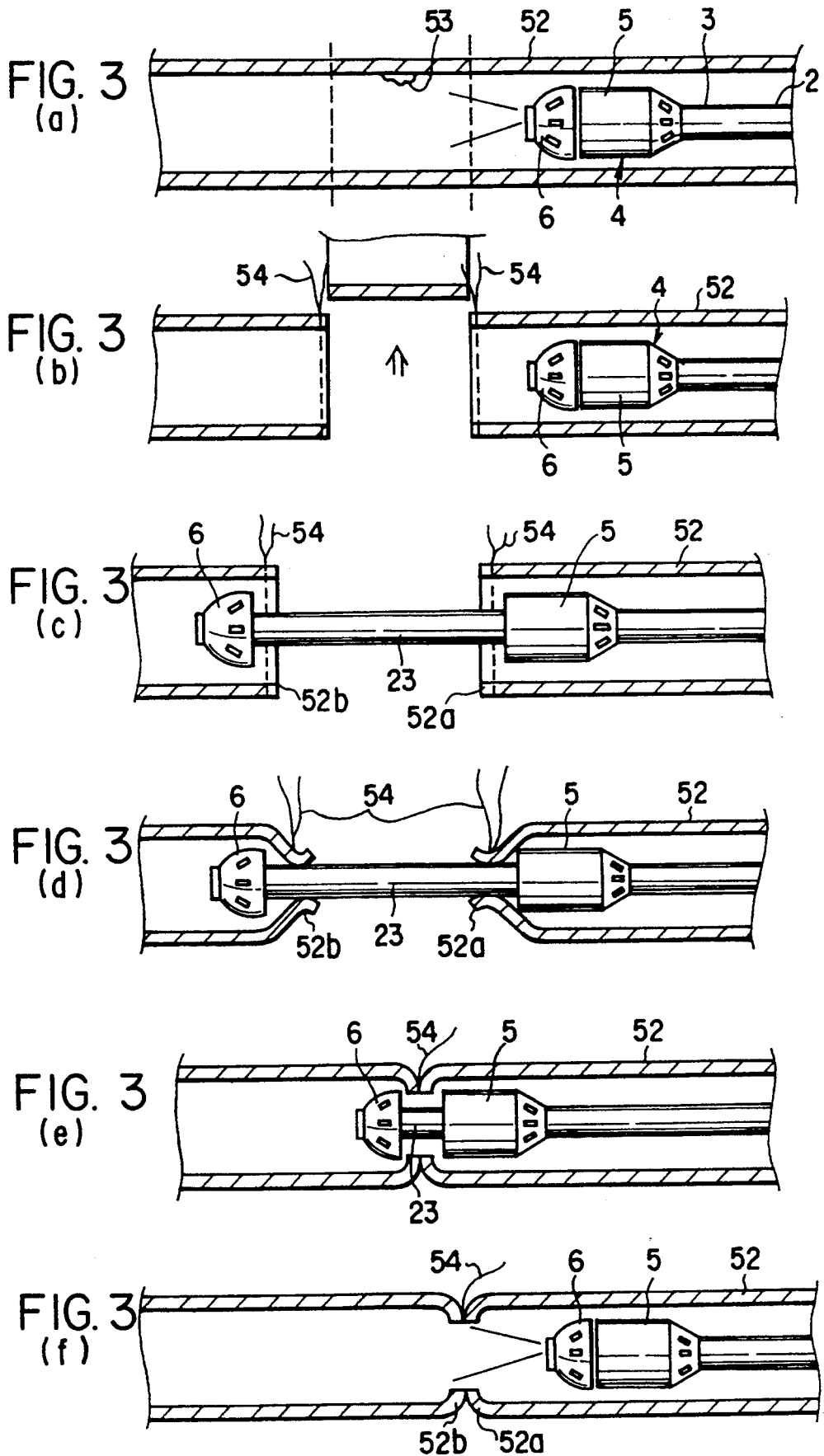

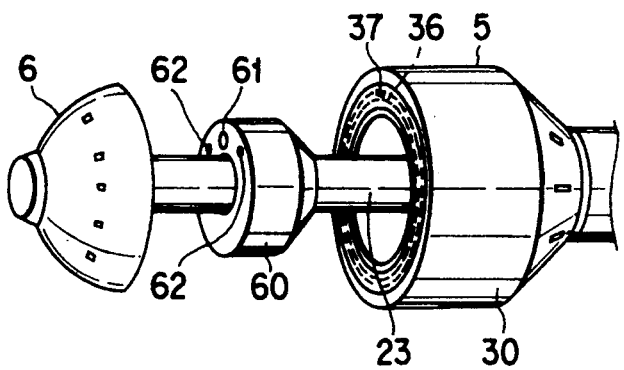
F I G. 5
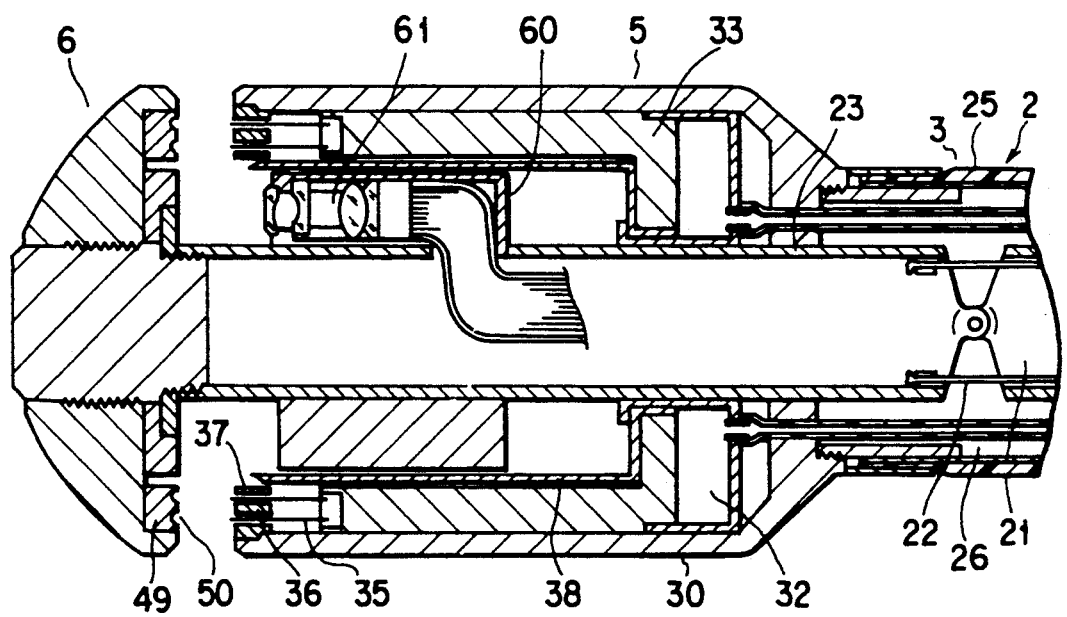
F I G. 6
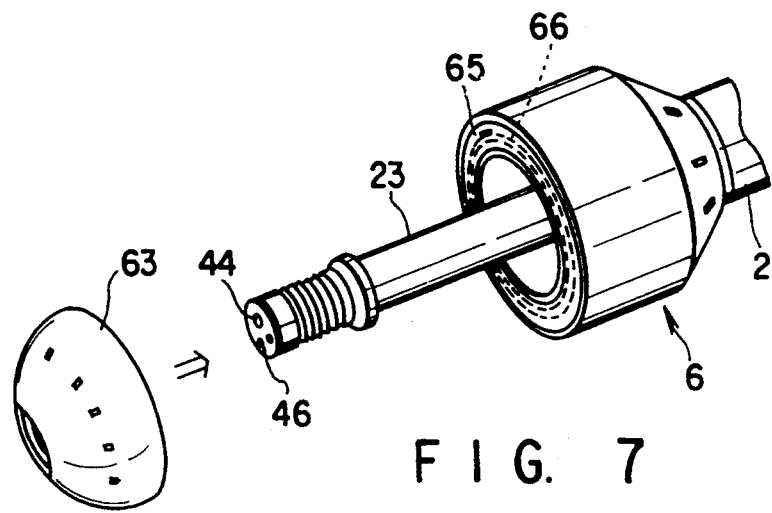
F I G. 7

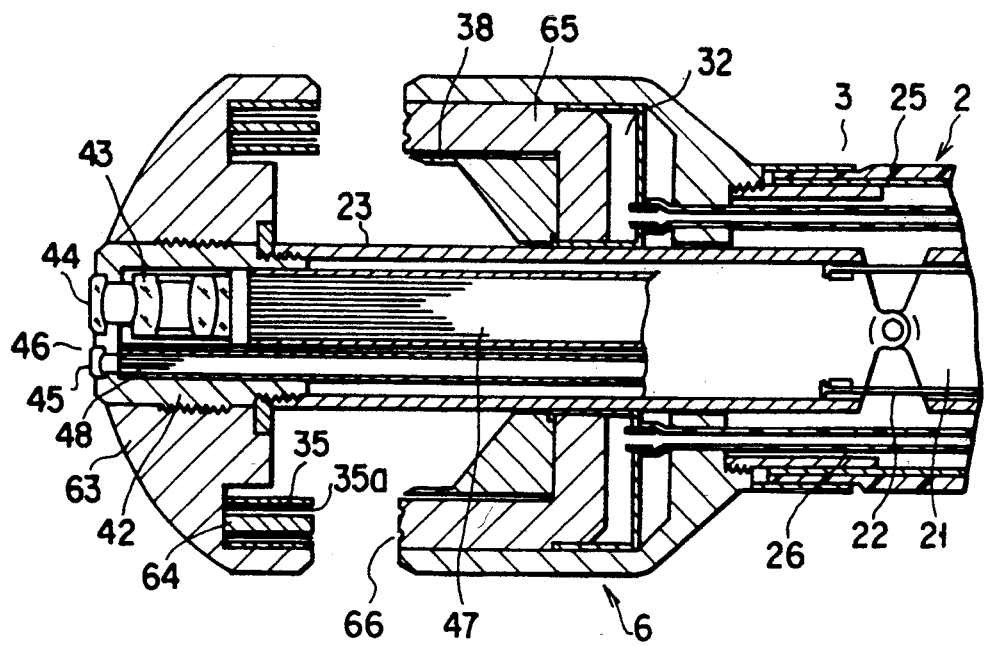
F I G. 8
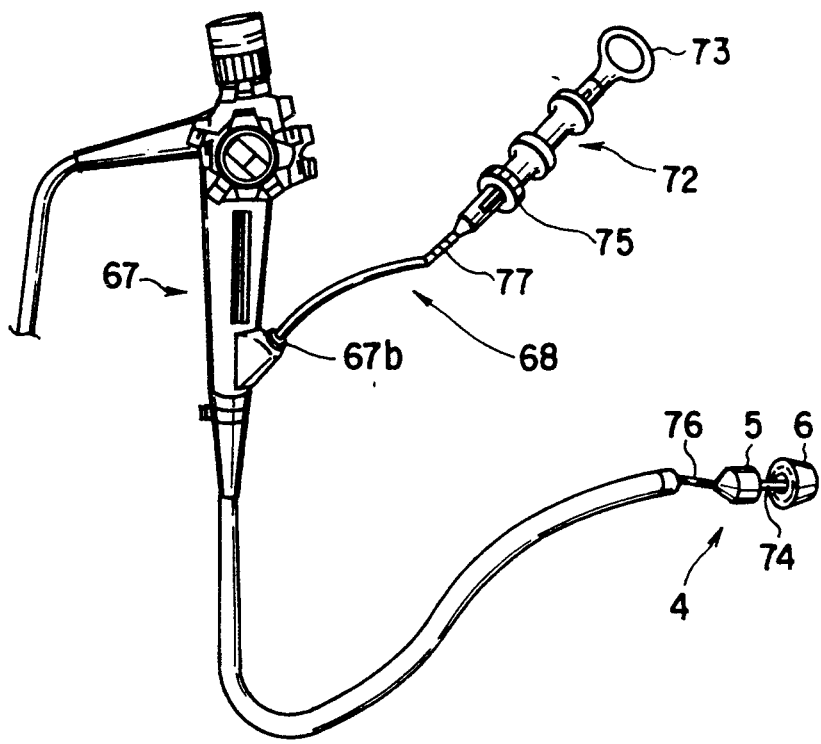
F I G. 9

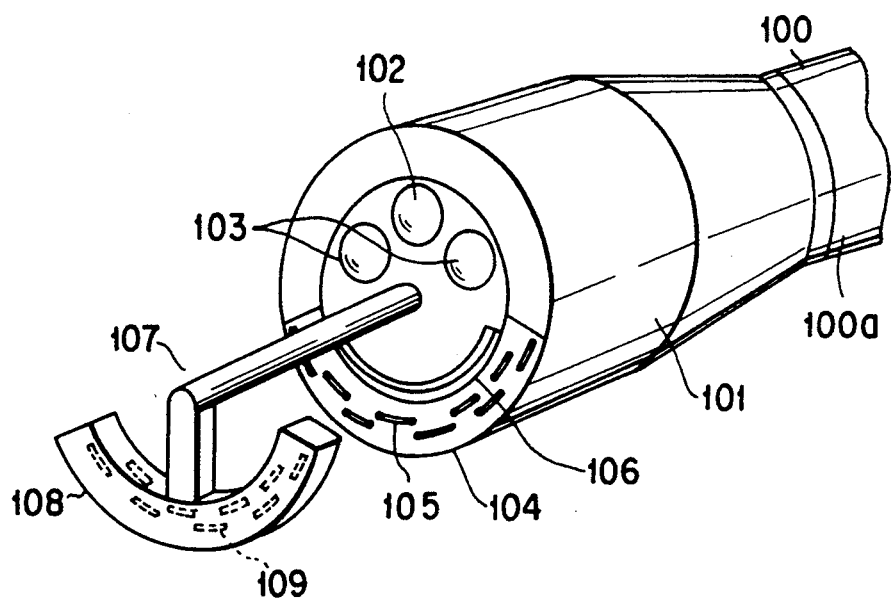
F I G. 15
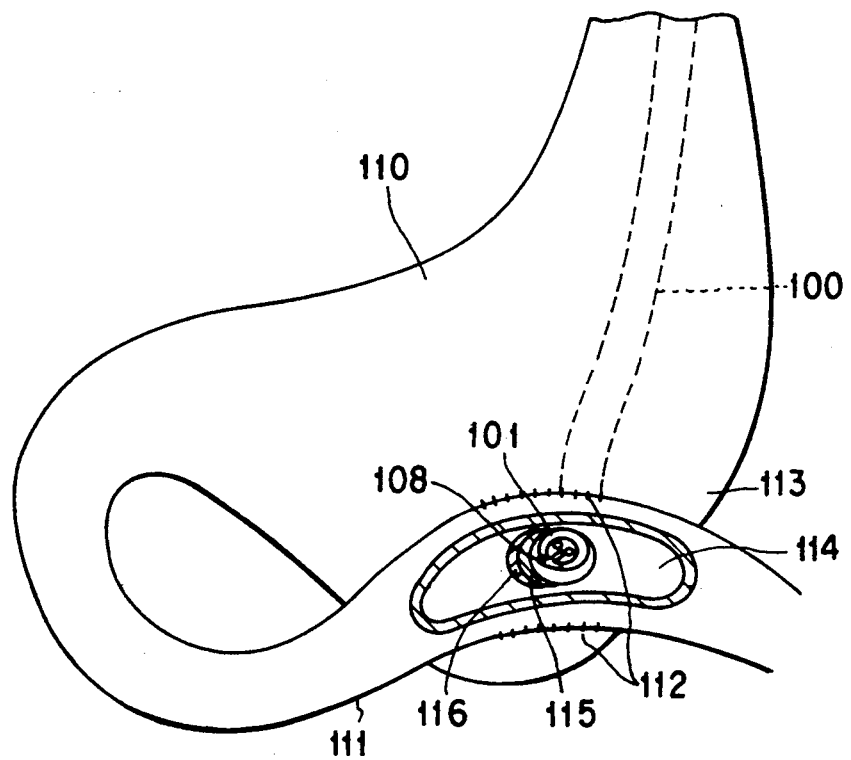
F I G. 16

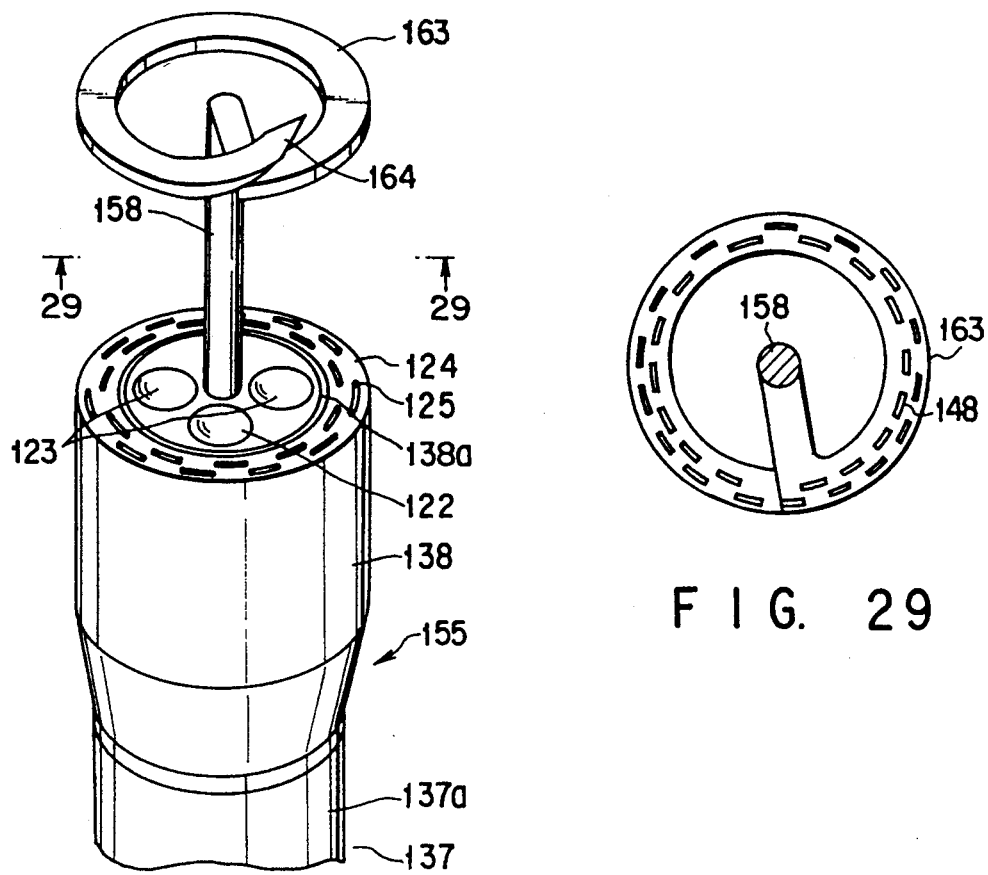
FIG. 28
FIG. 29
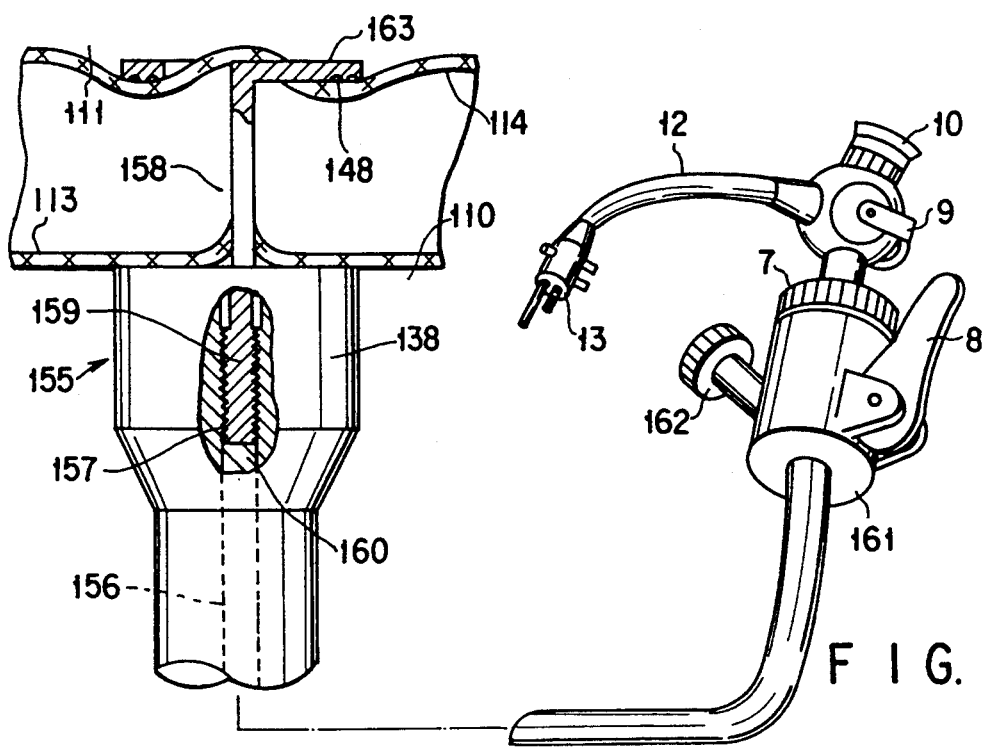
FIG. 30

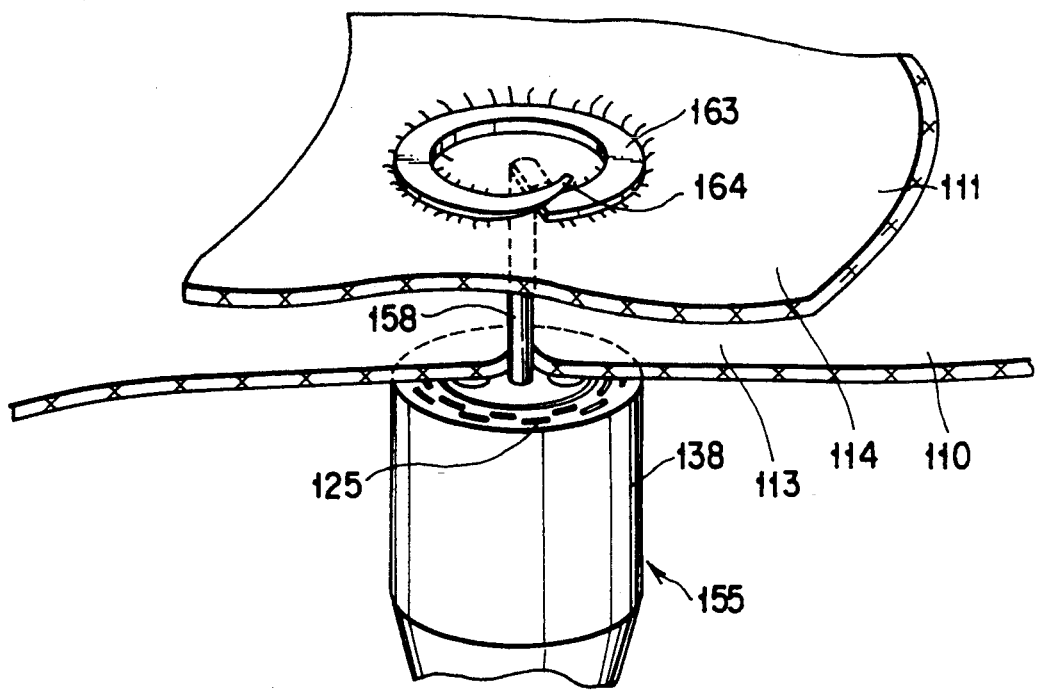
F I G. 31
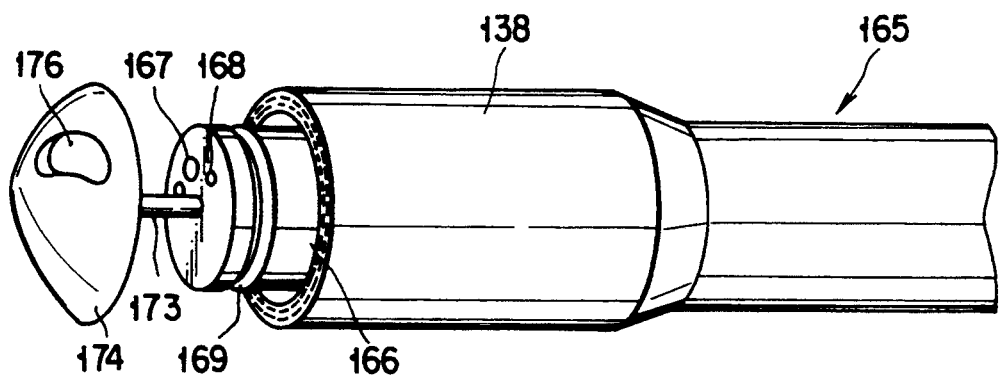
F I G. 33

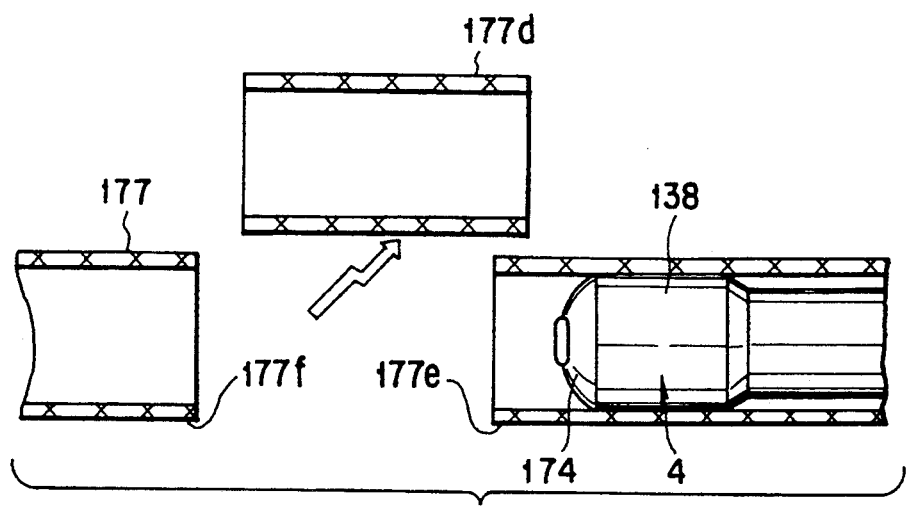
FIG. 37 (a)
FIG. 37 (b)
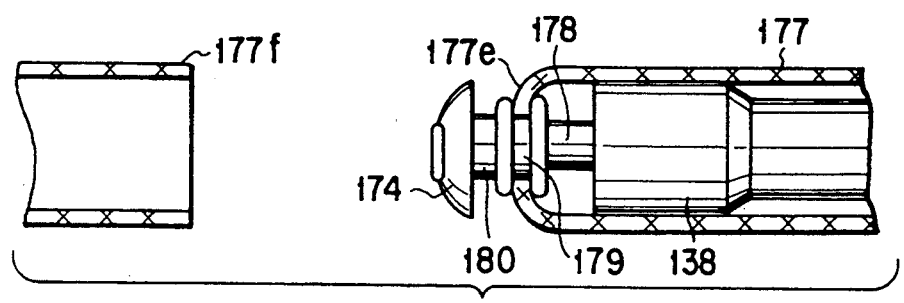
FIG. 37 (c)
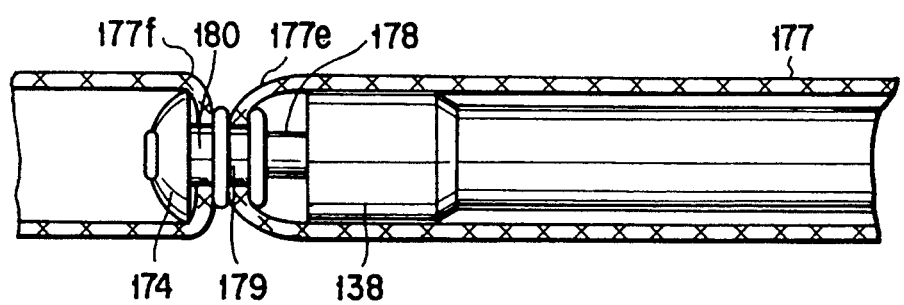
FIG. 37 (d)
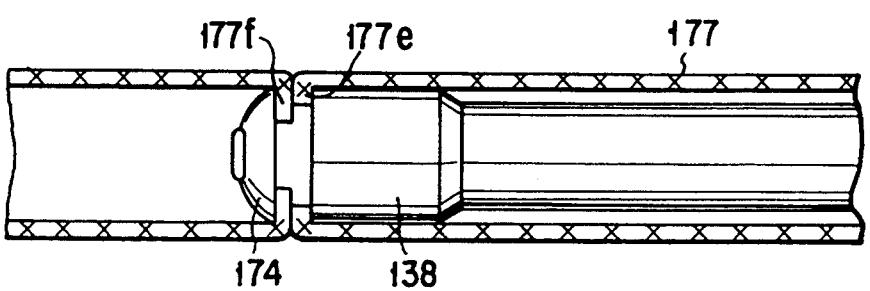
FIG. 37 (e)
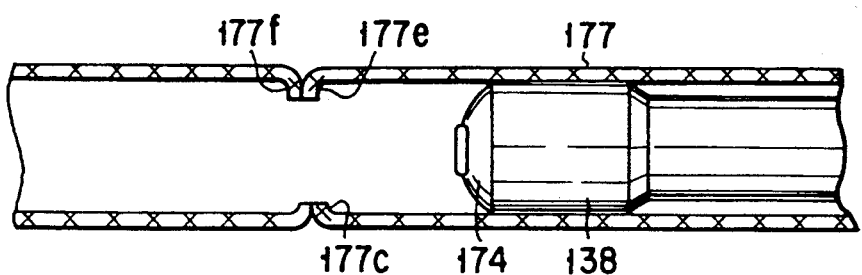

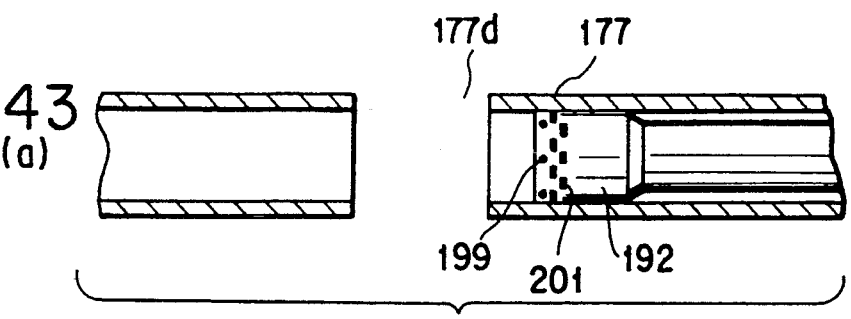
FIG. 43 (a)
FIG. 43 (b)
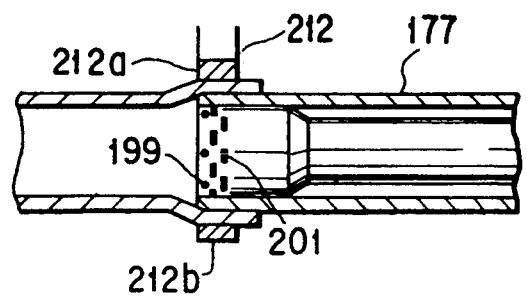
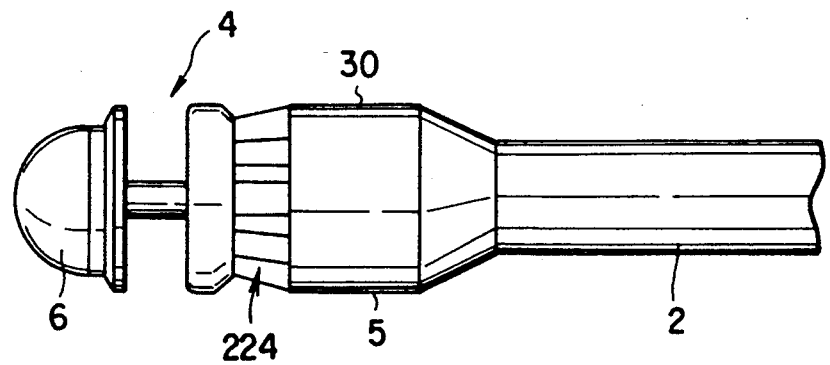
FIG. 45
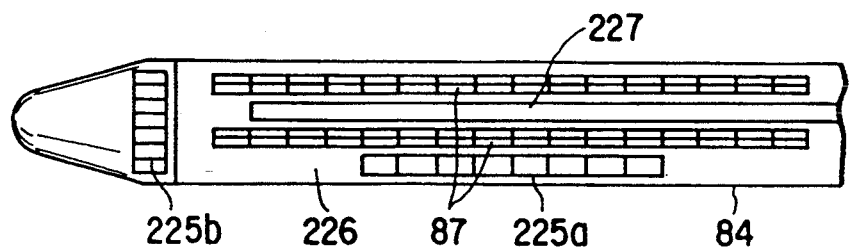
FIG. 46

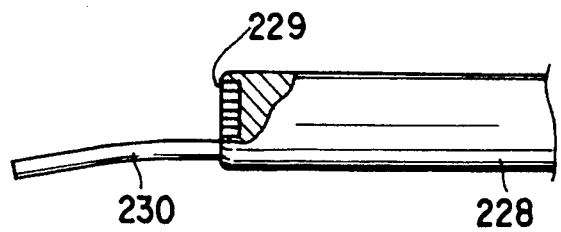
F I G. 47
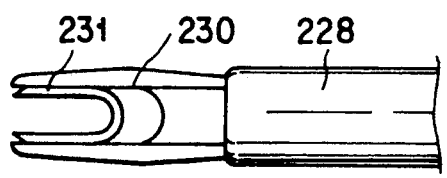
F I G. 48
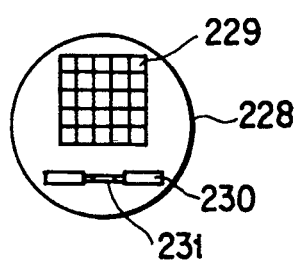
F I G. 49
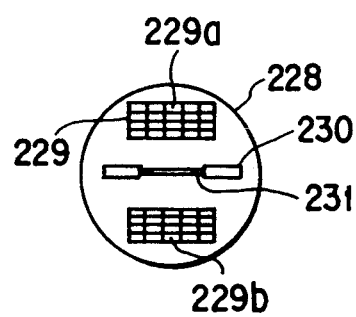
F I G. 50
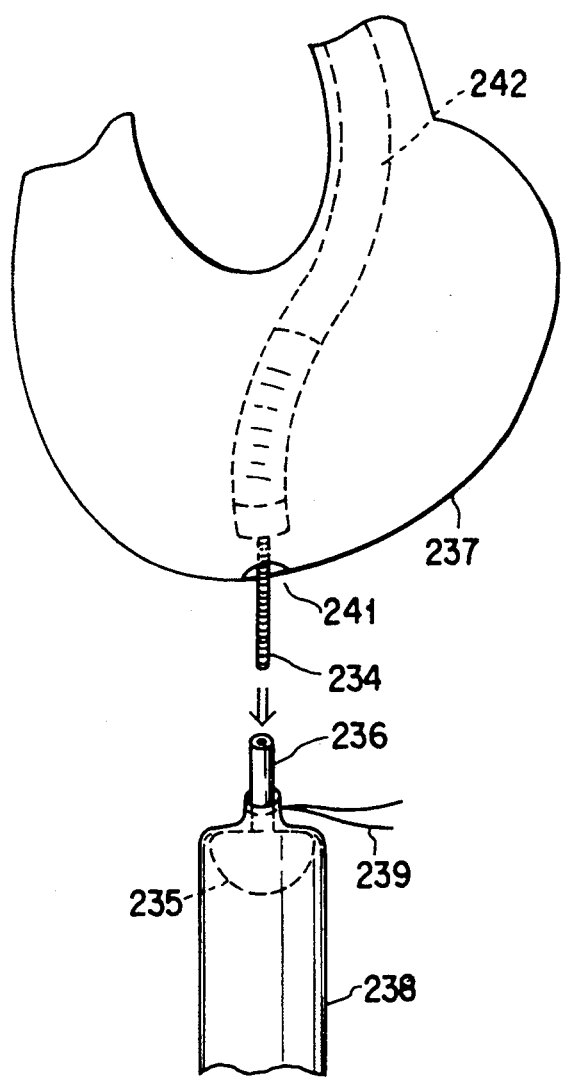
F I G. 51

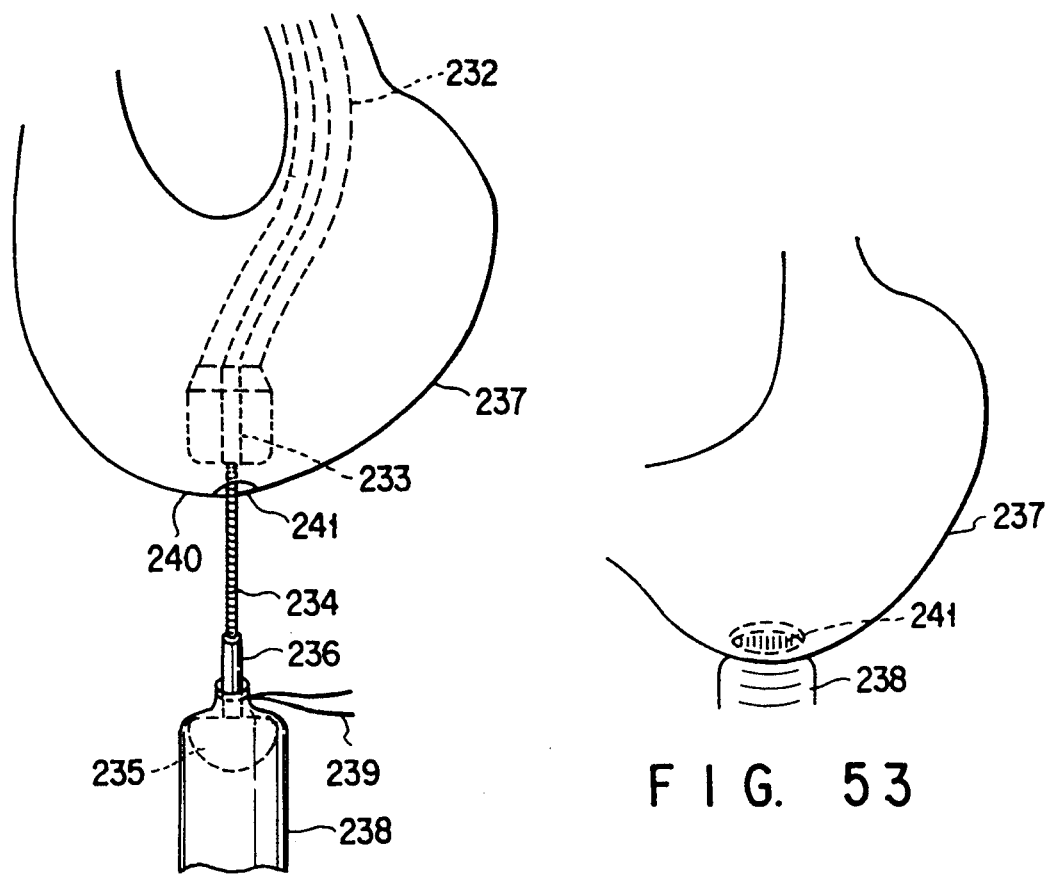
FIG. 52
FIG. 53
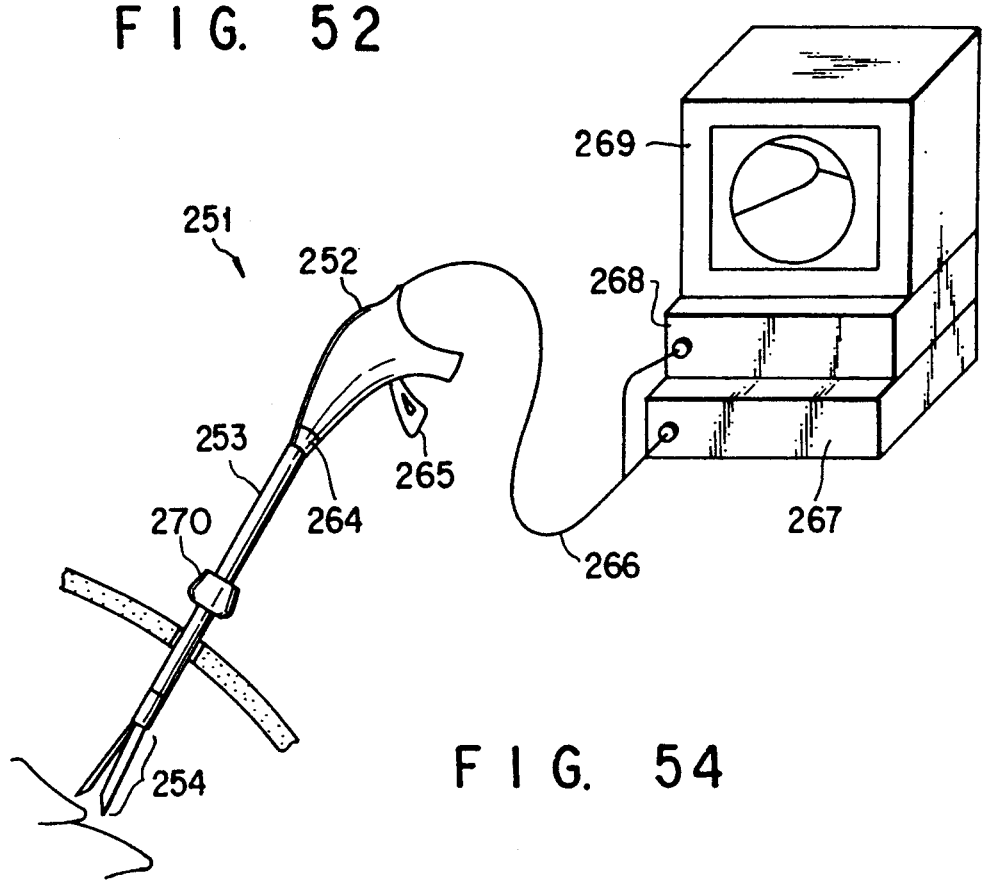
FIG. 54

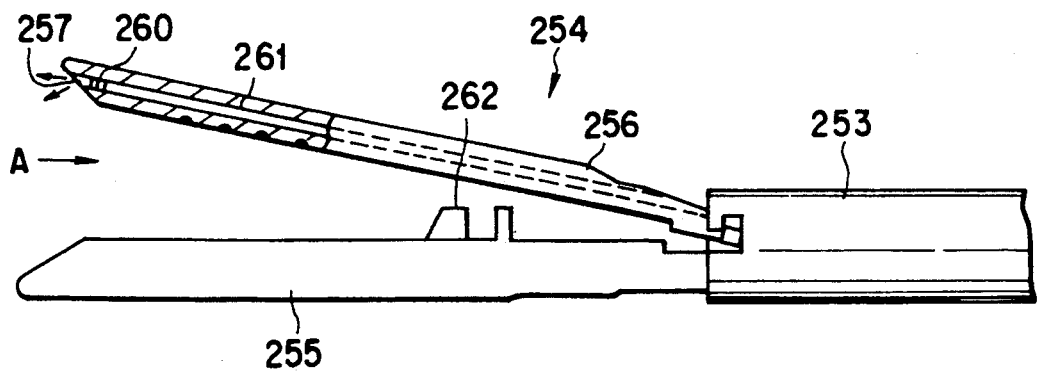
F I G. 55
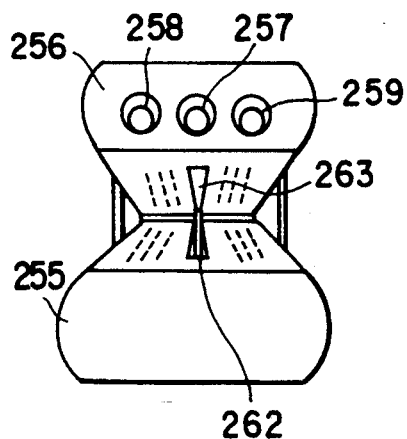
F I G. 56
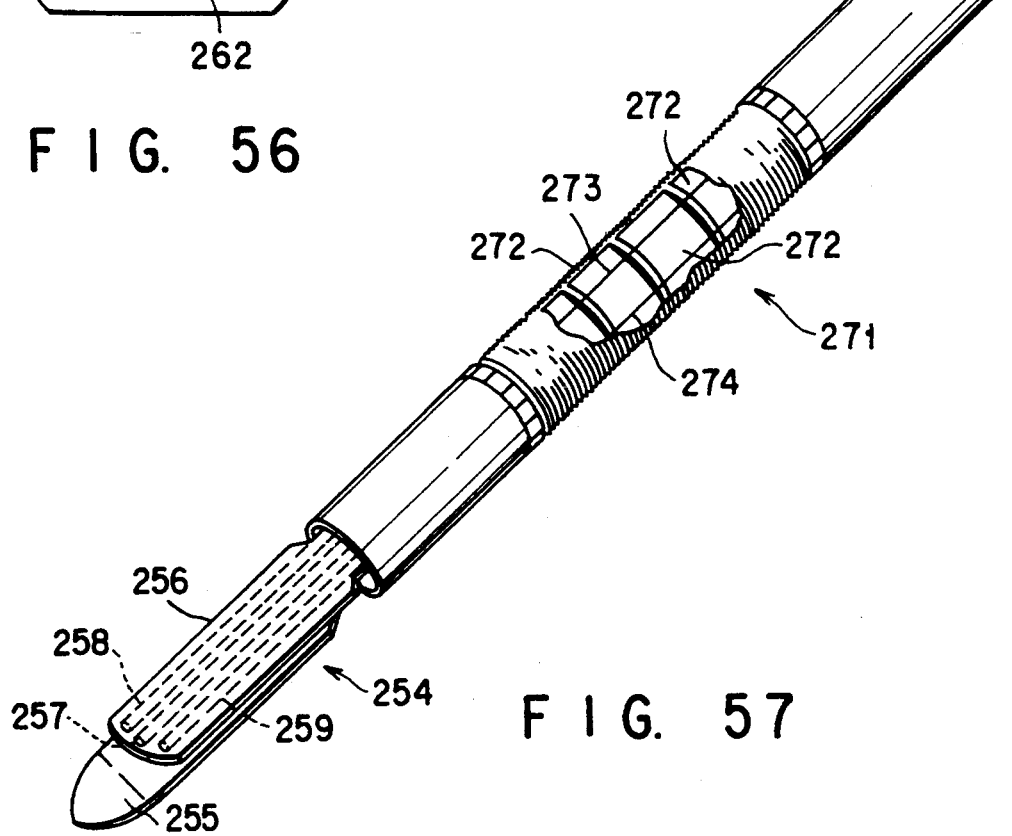
F I G. 57

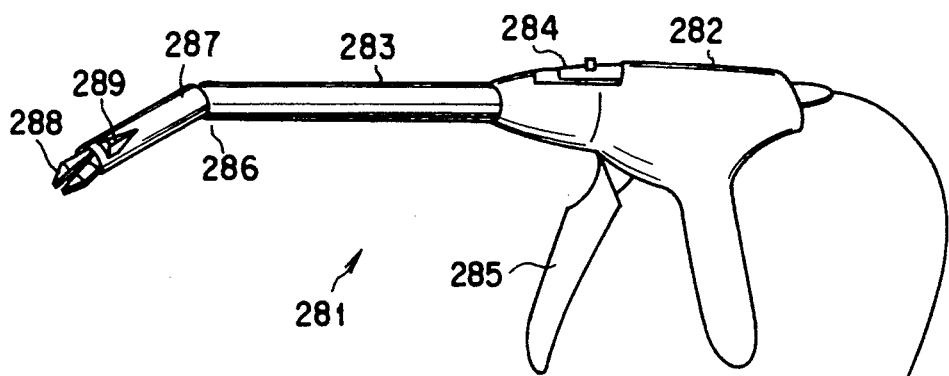
FIG. 58A
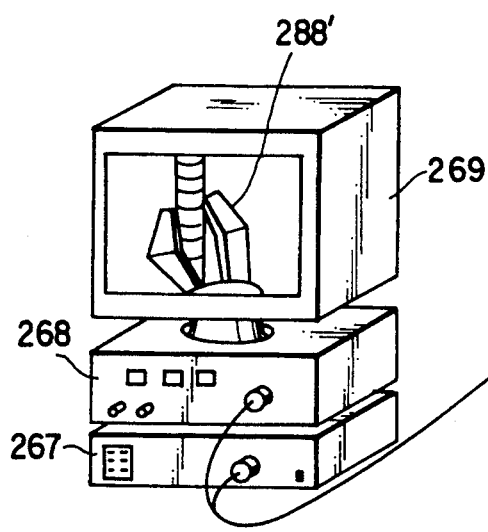
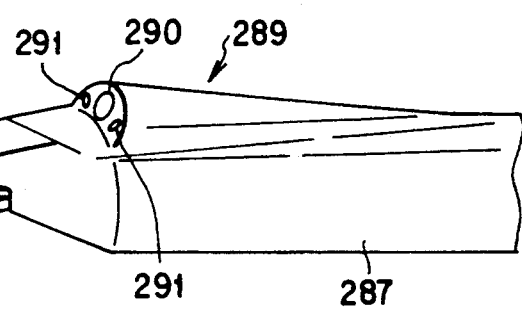
FIG. 58B
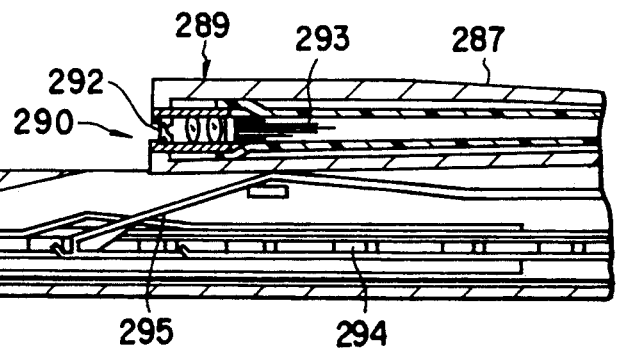
FIG. 58C

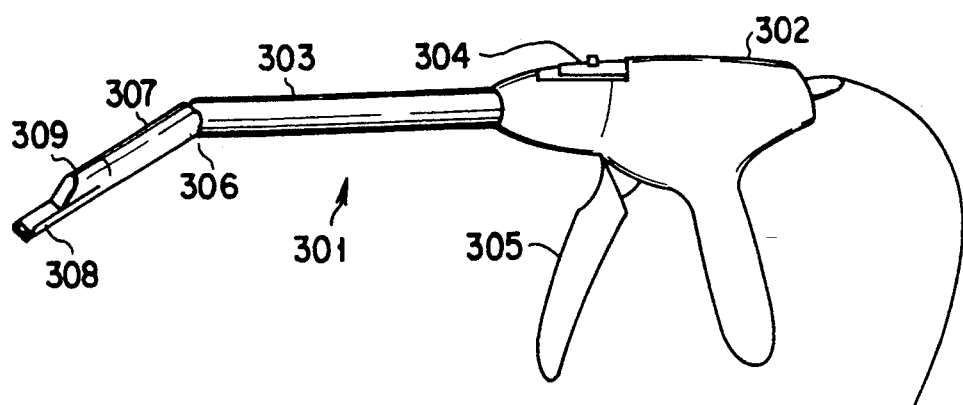
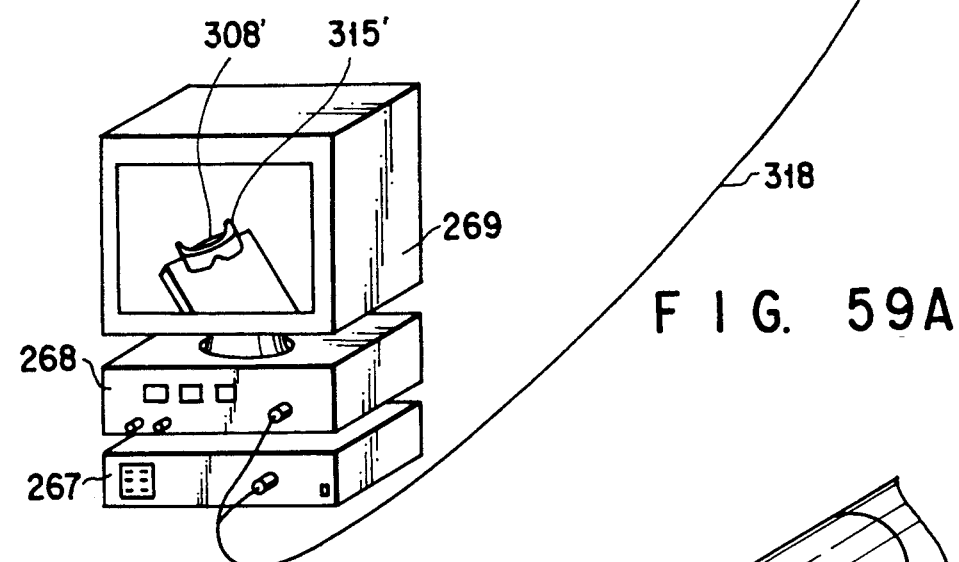
FIG. 59A
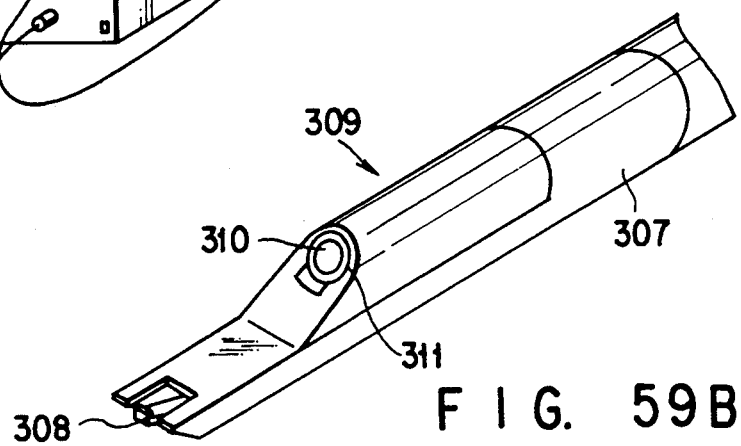
FIG. 59B
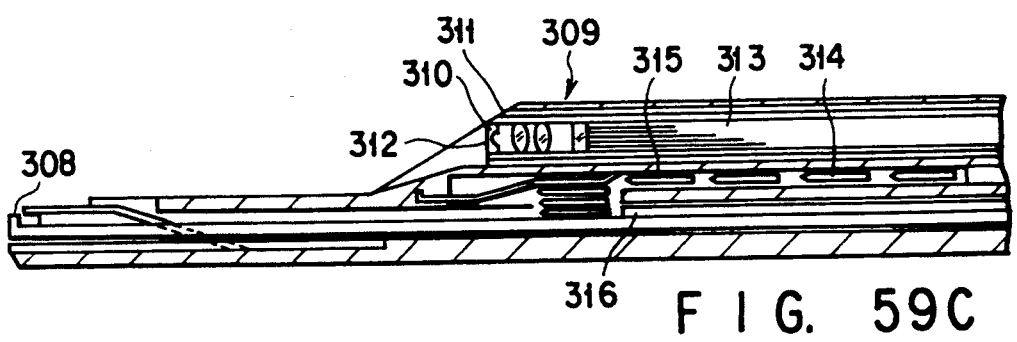
FIG. 59C

SURGICAL DEVICE FOR STAPLING AND FASTENING BODY TISSUES

BACKGROUND OF THE INVENTION

1. Field of the Invention

The present invention relates to a surgical device for stapling and fastening body tissues, more specifically the severed edges of tubular organs such as the large intestine or the small intestine.

2. Description of the Related Art

Tissue stapling/fastening devices are known which are designed to stitch together the severed edges of two normal portions of a tubular organ such as the large intestine, the small intestine or the duodenum, after a diseased portion of the organ has been excised. A device of this type makes it easy for a surgeon to apply staples or a suture ring, stitching together the normal portions of the organ. Thus, the device helps to shorten the time required for a surgical operation.

The tissue stapling/fastening device has an insertion section comprising a shaft which can be inserted into a tubular organ such as the large intestine. The distal end portion of the insertion section can hold staples or a suture ring. The insertion section is rigid, either straight or curving.

The rigid insertion section can hardly be inserted into a curving tubular organ such as the large intestine or the small intestine. If it is inserted into the tubular organ, it cannot reach the deepest portion of the organ. To stitch a deep portion of the organ, the organ is incised at a portion near the target portion of the organ, and the insertion section is inserted through the incision into the target portion. This is a complex operation.

New types of tissue stapling/fastening devices have been developed. Published Unexamined Japanese Patent Application No. 63-305854 discloses a device in which a flexible shaft connects the operation section and the stapling section. The operation section has a means for maintaining the shaft in a bent state. Published Unexamined Japanese Patent Application No. 59-501777 (WO 84/01095) discloses a similar device, in which hydraulic power is applied from the operation section to the stapling section to deform staples and excise unnecessary tissues.

To stitch together the severed edges of the portions of a tubular organ located near the anus, such as the rectum or the sigmoid colon, the insertion section of the device may be inserted through the anus. It is difficult, however, to guide the distal end of the insertion section to any position deeper than rectum or the sigmoid colon. To excise the diseased portion of the large intestine by using a laparoscope, without forming an incision in the abdominal wall, it would be impossible to insert the insertion section of a tissue stapling/fastening device.

In the device disclosed in Published Unexamined Japanese Patent Application No. 63-305854, the shaft is bent due to the resistance of the inner surface of the organ as it is inserted into the cavity in that organ, in order to excise the organ. Therefore, the shaft can hardly be bent in the same way as does the curving portion of the organ, and cannot smoothly pass therethrough. Consequently, it would be difficult to insert the shaft into the organ.

In the device disclosed in Published Unexamined Japanese Patent Application No. 59-501777, the shaft must be bent in accordance with the resistance of the inner surface of the organ until the stapling section reaches the tissues in the organ. The shaft must be rigid enough to transmit a force for stitching the tissues and a force for excising unnecessary parts of the tissues within an organ. Because of its rigidity, however, the shaft can hardly be bent or deformed complementary to the curving inner surface of the organ.

With either tissue stapling/fastening device, to insert the stapling section into the organ to reach the target tissues existing therein, it is necessary to incise that part of the organ wall which is near the target tissues, thereby forming an opening large enough to allow the passage of the stapling section into the organ. The opening must of course be stitched and closed after the completion of the intra-organ surgical treatment. Thus, to incise the wall of the organ for the purpose of inserting the stapling section into the organ is undesirable in view of the pain and discomfort the patient will inevitably suffer.

When the severed edges c of two parts of an intestine a (e.g., the large intestine) are stitched together with staples b, as shown in FIG. 61, by means of the conventional tissue stapling/fastening device, the edges c are located inside the intestine a. From the outer appearance of the intestine a, it is impossible to determine whether or not the parts of the intestine a have been stitched steadfastly.

SUMMARY OF THE INVENTION

Accordingly, the object of the present invention is to provide a surgical device for stapling and fastening body tissues, which can be smoothly inserted into a body cavity, easily guiding staples or fasteners to the target body tissues, and can monitor not only the interior of the organ but also the state the tissues assume immediately after they have been connected by the staples or fasteners.

According to the present invention, there is provided a surgical device for stapling and fastening body tissues, comprising: holding means for holding a plurality of stapling/fastening members; applying means located in the holding means, for applying the stapling/fastening members to the body tissues; deforming means for deforming the stapling/fastening members, thereby to staple or fasten the body tissues together; an operation section for operating the deforming means; observation means located near the deforming means; and display means for displaying images supplied from the observation means.

A surgeon can insert the distal end portion of the surgical device into a body cavity and guides the stapling/fastening members to target tissues, while seeing the image of the interior of the body cavity, which the display means is displaying. Then, he or she operates the operation section, driving the applying means. The applying means applies the stapling/fastening members to the tissues, and the deforming means deforms the members, thereby stapling or fastening the tissues together.

The observation means enables a surgeon to see the image of the interior of an organ, while inserting the distal end portion of the device into that organ. Thus, the surgeon can smoothly guide the stapling/fastening members to a desired position, and can visually examine how the members have been applied.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 2 is a perspective view of the surgical stapler;

FIGS. 3(a)-3(f) show diagrams explaining how the stapler is operated to stitch together the severed edges of two portions of the large intestine;

FIG. 5 is a perspective view of a surgical stapler according to a second embodiment of this invention;

FIG. 6 is a sectional side view showing the stapling member of the stapler shown in FIG. 5;

FIG. 7 is a perspective view of a surgical stapler according to a third embodiment of this invention;

FIG. 8 is a sectional side view showing the stapling member of the stapler shown in FIG. 7;

FIG. 9 is a perspective view of a surgical stapler which is a fourth embodiment of the present invention;

FIG. 15 is a perspective view of the distal end portion of a stapler/endoscope which is a sixth embodiment of this invention;

FIG. 16 is a perspective view for explaining how the stapler/endoscope is operated to staple the duodenum to the stomach;

FIG. 28 is a perspective view of a stapler/endoscope according to a tenth embodiment of the present invention;

FIG. 29 is a cross sectional view, taken along line 29—29 of FIG. 28;

FIG. 30 is a diagram explaining how the anvil of the stapler/endoscope shown in FIG. 28 is inserted into the stomach, piercing the wall of duodenum and the wall of the stomach;

FIG. 31 is a perspective view, explaining how the anvil is inserted into the stomach, piercing the wall of duodenum and the wall of the stomach;

FIG. 33 is perspective view of the distal end portion of the stapler/endoscope shown in FIG. 32;

FIGS. 37(a)-37(e) show diagrams explaining how the stapler/endoscope of FIG. 36 is operated;

FIGS. 43(a) and 43(b) show diagrams explaining how the stapler/endoscope of FIG. 38 is operated;

FIG. 45 is a side view showing the distal end portion of a stapler according to a fifteenth embodiment of the present invention;

FIG. 46 is a plan view of the anvil of a stapling member incorporated in a sixteenth embodiment of this invention;

FIG. 47 is a cutaway side view of the distal end portion of a stapler according to a seventeenth embodiment of the present invention;

FIG. 48 is a plan view of the insertion section of the stapler shown in FIG. 47;

FIG. 49 is a front view of the insertion section of the stapler shown in FIG. 47;

FIG. 50 is a front view of a modification of the insertion section shown in FIG. 49;

FIG. 51 is a diagram explaining how to use a stapler according to an eighteenth embodiment of the invention;

FIG. 52 is another diagram explaining how to use the stapler shown in FIG. 51;

FIG. 53 is a perspective view showing the stomach and the small intestine which are stapled together by means of the stapler shown in FIG. 51;

FIG. 54 is a diagram schematically illustrating a stapler/endoscope according to a nineteenth embodiment of the present invention;

FIG. 55 is a cutaway side view showing the distal end portion of the stapler/endoscope shown in FIG. 54;

FIG. 56 is a front view of the distal end portion, as seen in the direction of arrow A in FIG. 55;

FIG. 57 is a perspective view of a stapler/endoscope according to a twentieth embodiment of the present invention;

FIG. 58A is a diagram schematically showing a clip applicator/endoscope according to a twenty-first embodiment of the present invention;

FIG. 58B is a perspective view showing the distal end portion of the clip applicator/endoscope;

FIG. 58C is a sectional side view of the distal end portion shown in FIG. 58B;

FIG. 59A is a diagram schematically showing a stapler/endoscope according to a twenty-second embodiment of the present invention;

FIG. 59B is a perspective view showing the distal end portion of the stapler/endoscope shown in FIG. 59A;

FIG. 59C is a sectional side view of the distal end portion shown in FIG. 59B;

DETAILED DESCRIPTION OF THE PREFERRED EMBODIMENTS

Figure 1:
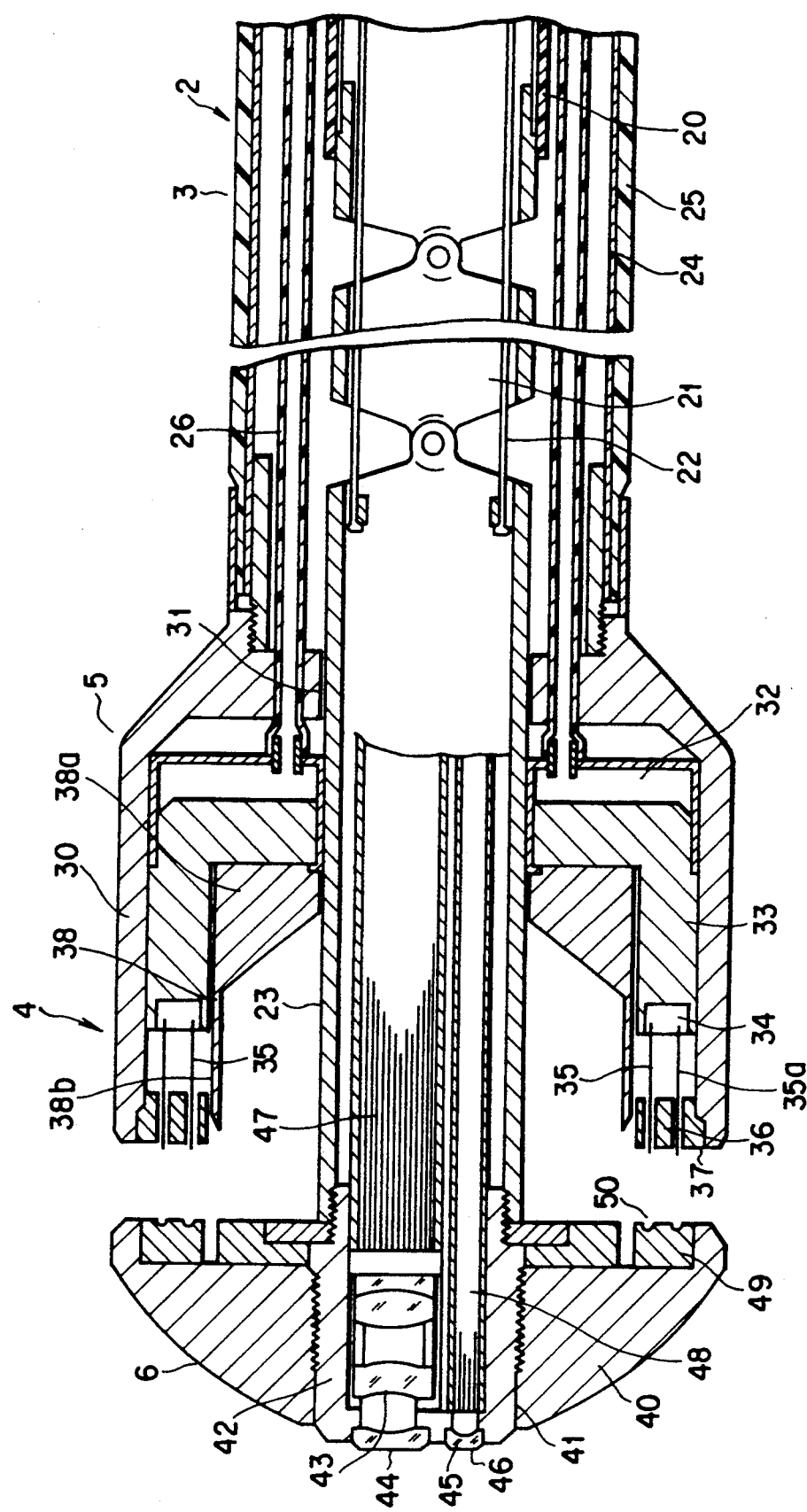
FIG. 1 is a sectional side view showing the stapling member of a surgical stapler according to a first embodiment of the present invention.

Embodiments of the present invention will now be described, with reference to the accompanying drawings. FIGS. 1 to 4B show a first embodiment of the invention which is a surgical stapler. As shown in FIG. 2, the stapler comprises an operation section 1 and an insertion section 2. The insertion section 2 has a flexible portion, a bendable portion 3 and a stapling member 4. The stapling member 4 is connected to the bendable portion 3. The member 4 comprises a staple applier 5 for applying staples to body tissues, and an anvil 6 for deforming the staples applied to the tissues.

The operation section 1 has an operating knob 7 and a pusher/cutter driving lever 8. Coupled to the operation section 1 are a lever 9, an ocular 10, an air/water supply button 11, and a universal cord 12. The universal cord 12 is connected at its free end to a connector 13, which is to be connected to a light source (not shown).

With reference to FIG. 1, the insertion section 2 will be described in detail. An operating tube 20 extends through the insertion section 2; it can be moved along its axis and can be rotated around its axis.

The bendable portion 3 has several hollow cylindrical bending segments 21 which are rotatably connected to each other by a pin. The proximal segment 21 is connected to the operating tube 20. The distal segment 21 is rotatably connected to a rigid tubular shaft 23 by a pin. The tube 23 extends through the staple applier 5 along the axis thereof. A pair of operating wires 22 extend through the operating tube 20 and the hollow cylindrical bending segments 21 and are fastened to the rear end of the rigid tubular shaft 23. The anvil 6 is fastened to the distal end of the rigid tubular shaft 23, in screw engagement.

The operating tube 20 and the hollow cylindrical bending segments 21 are surrounded by a helical tube 24, which in turn is covered by an outer sheath 25. Several hydraulic tubes 26 extend through the space between the outer circumference of the tube 20 and the segments 21, on the one hand, and the inner circumference of the helical tube 24. Each hydraulic tube 26 communicates at its proximal end with a hydraulic cylinder (not shown) which is driven by operating the pusher/cutter driving lever 8.

A housing 30 of the staple applier 5 is sutured to the distal end of the insertion section 2. The housing 30 is a hollow cylinder opening at its front end and has an opening 31 in its rear end. The rigid tubular shaft 23 is inserted in this opening 31 and can move back and forth along its axis.

The rigid tubular shaft 23 and the housing 30 define an annular space 32 which communicates with the hydraulic tubes 26. A staple pusher 33 which is similar in shape to the housing 30 is located within the annular space 32 and can move back and forth.

A staple-holding groove 34, which is an annular groove, is formed in the front end of the staple pusher 33. Staples 35 are arranged in the groove 34 in two circles. The staples 35 have been prepared by bending thin wires in the form letter U. Each staple 35 is positioned, with its head lying on the bottom of the staple-holding groove 34 and its legs 35a extending forward.

An annular plate 36 is fastened to the distal end of the housing 30. The plate 36 has a plurality of slits 37 arranged in two circles. Through these slits 37, the staples 35 will be applied to body tissues as the staple pusher 33 is thrust forward.

A cutter 38 is located in the staple pusher 33, fixed to the inner rear surface thereof. The cutter 38 comprises an annular base 38a secured to the staple pusher 33 and an annular blade 38b coaxial with the base 38a and extending forward therefrom. The cutter 38 moves back and forth along with the staple pusher 33.

The anvil 6 comprises an anvil body 40 which is shaped like a rounded cone and which has a center through hole 41. A hollow cylinder 42 is fitted in the hole 41 in screw engagement. The distal end portion of the cylinder 42 is fitted in the rigid tubular shaft 23 in screw engagement therewith, whereby the anvil 6 is fastened to the rigid tubular shaft 23.

The hollow cylinder 42 contains an optical system which comprises an objective 43, an observation window 44 located in front of the objective 43, a light-applying lens 45, and an illumination window 46 located in front of the lens 45. The objective 43 is optically connected to an image-transmitting fiber 47. The light-applying lens 45 is optically connected to a light-guiding fiber 48. The image-transmitting fiber 47 extends to the operation section 1 through the rigid tubular shaft 23, the hollow cylindrical bending segments 21, and the operating tube 20, and its proximal end is coupled to the ocular 10. The light-guiding fiber 48 extends to the operation section 1 through the rigid tubular shaft 23, the segments 21, and the operating tube 20, and is connected to the universal cord 12.

A ring-shaped anvil member 49 is fitted in a recess made in the back of the anvil body 40. The anvil member 49 has two annular grooves 50 formed in its surface. The annular grooves 50 are concentric with the two circles of slits 37 formed in the annular plate 36 of the staple applier 5, respectively.

As shown in FIG. 2, the anvil body 40 has air/water supplying nozzles 51 formed in the front face. The nozzles 51 are connected to the air/water supply button 11 of the operation section 1 by an air/water supplying tube (not shown) which extends through the insertion section 2.

The stapler shown in FIGS. 1 and 2 is operated as follows. First, the lever 9 is operated, pulling one operating wire 22 and slacking the other operating wire 22. The bendable portion 3 of the insertion section 2 is thereby bent in a desired direction. As a result, the stapling member 4 is directed to a desired position.

While the insertion section 2 is inserted in a body organ, the light source (not shown) is kept on, applying light into the organ through the light-guiding fiber 48, the light-applying lens 45, and the illumination window 46. The light reflected from the interior of the organ is applied to the ocular 10 through the observation window 44, the objective 43, and the image-transmitting fiber 47. Hence, a surgeon can insert the section 2 deeper into the organ, while seeing the image of the interior of the organ.

When the air/water supply button 11 is pushed, air or physiological saline is supplied to target tissues through the air/water supplying nozzles 51 formed in the front of the anvil body 40.

As the operating knob 7 is rotated, the operating tube 20, the segments 21 and the rigid tubular shaft 23 are pulled and pushed. The anvil 6, which is fastened to the rigid tubular shaft 23, is thereby moved back and forth along the axis of the insertion section 2. Thus, the anvil 6 moves toward and away from the staple applier 5, whereby the gap between the staple applier 5 and the anvil 6 can be adjusted in accordance with the thickness of target tissues.

When the pusher/cutter driving lever 8 is squeezed, a hydraulic medium is pumped into the annular space 32 through the hydraulic tubes 26, raising the pressure in that space 32. The stapler pusher 33 is thereby thrust forward, pushing the staples 35 forward from the staple-holding groove 34 through the slits 37 which are formed in the annular plate 36 of the staple applier 5. Hence, when the lever 8 is squeezed after the target tissues are clamped together between the staple applier 5 and the anvil 6, the legs 35a of each staple 35 will pierce the tissues, then abut on the bottom of the annular grooves 50 of the anvil member 49, and are finally bent toward each other. As a result of this, the staples 35 stitch the tissues together, forming two circular seams.

At the same time the stapler pusher 33 is thrust forward, the cutter 38, which is secured to the pusher 33, is moved forward, excising the those parts of the tissues which are inside the inner circular seam.

Hence, the tissues can be stitched together and the unnecessary parts thereof can be cut off at the same time, merely by squeezing the pusher/cutter driving lever 8 after the tissues have been clamped between the staple applier 5 and the anvil 6. The severed edges of the tissues stitched with the staples 35 form a neat and smooth rim.

With reference to FIG. 3, it will be explained how the stapler of FIGS. 1 and 2 is manipulated to stitch together the severed edges of two portions of the large intestine.

As shown in step (a) in FIG. 3, a surgeon inserts the stapling member 4 into the large intestine 52 through the anus, while applying light into the large intestine 52 via the light-guiding fiber 48, the lens 45, and the window 46. The light reflected from the interior of the intestine 52 is applied to the ocular 10 through the window 44, the objective 43, and the image-transmitting fiber 47. Hence, seeing the interior of the intestine 52 through the ocular 10, the surgeon operates the lever 9, bending the bendable portion 3 of the insertion section 2 and thereby guiding the stapling member 4 through the intestine 52 until the member 4 reaches a position near the diseased portion of the large intestine 52.

Then, the surgeon forms an incision in the abdominal wall, inserts a laparoscope into the abdomen through that incision, and excises the diseased portion 53 of the intestine 52 by using a cutter inserted into the abdomen through the laparoscope, as is illustrated steps (a) and (b) in FIG. 3. Alternatively, he or she may form a large cut in the abdominal wall, exposing the large intestine 52, and then cut off the diseased portion 53 of the intestine 52. Thereafter, the surgeon applies a tying thread 54 to each severed end of the intestine 52 as shown step (b) in FIG. 3.

Thereafter, as shown step (c) in FIG. 3, the surgeon inserts the stapling member 4 deeper in the large intestine 52 until it reaches the severed end 52a of the first normal portion of the intestine 52, as illustrated step (c) in FIG. 3. Then, he or she rotates the operating knob 7, thrusting the anvil 6 into the second normal portion of the intestine 52 through the severed end 52b thereof.

Next, as shown step (d) in FIG. 3, the tying threads 54 are pulled, squeezing and tying both severed ends 52a and 52b of the normal portions of the intestine 52 to the rigid tubular shaft 23. This done, the surgeon rotates the operating knob 7 in the opposite direction, pulling the anvil 6 back toward the staple applier 5. As a result, the second portion of the intestine 52 is pulled to the first portion of the intestine 52 as is shown step (e) in FIG. 3. At this time, the severed ends 52a and 52b of both portions of the intestine 52 are clamped between the staple applier 5 and the anvil 6.

In this condition, the surgeon squeezes the pusher/cutter driving lever 8, whereby the staple applier 5 applies the staples 35 to the clamped ends 52a and 52b of the portions of the intestine 52. The legs 35a of each staple 35 pierces the severed ends 52a and 52b, abut on the bottom of the annular grooves 50 of the anvil member 49, and finally are bent toward each other. Thus applied, the staples 25 stitch the tissues together, forming two circular seams. At the same time the stapler pusher 33 is thrust forward, the cutter 38 is moved forward, excising those parts of the severed ends 52a and 52b which are inside the inner circular seam.

Thereafter, as shown step (f) in FIG. 3, the surgeon pulls the insertion section 2, thus moving the stapling member 4 backward from the stapled ends 52a and 52b of the normal portions of the large intestine 52, while observing the stapled ends 52a and 52b and, thus, determining whether or not the severed ends 52a and 52b have been stitched together neatly and whether or not the stitched ends 52a and 52b have been excised appropriately. Finally, the surgeon pulls the stapling member 4 from the large intestine 52 through the anus, completing the operation of excising the diseased portion 53 of the intestine 52.

Since the stapling member 4 has an observation means, it is easy for the surgeon to guide the member 4 to a desired position in an organ, and is possible for him or her to determine whether or not the target tissues have been stapled properly and whether or not the unnecessary parts of the stapled tissues have been excised appropriately.

Since the insertion section 2 is flexible, the stapling member 4 can be smoothly inserted deep into a curving organ such as the large intestine. Further, since the member 4 can be inserted through the anus, no incision needs to be made in an organ located near the anus, such as the rectum, the sigmoid colon or the large intestine, for allowing the insertion of the stapling member 4. This helps to reduce the pain and distress on the part of the patient, and also enables the surgeon to observe the state the tissues assume right after they have been stapled and severed.

Figure 4A:
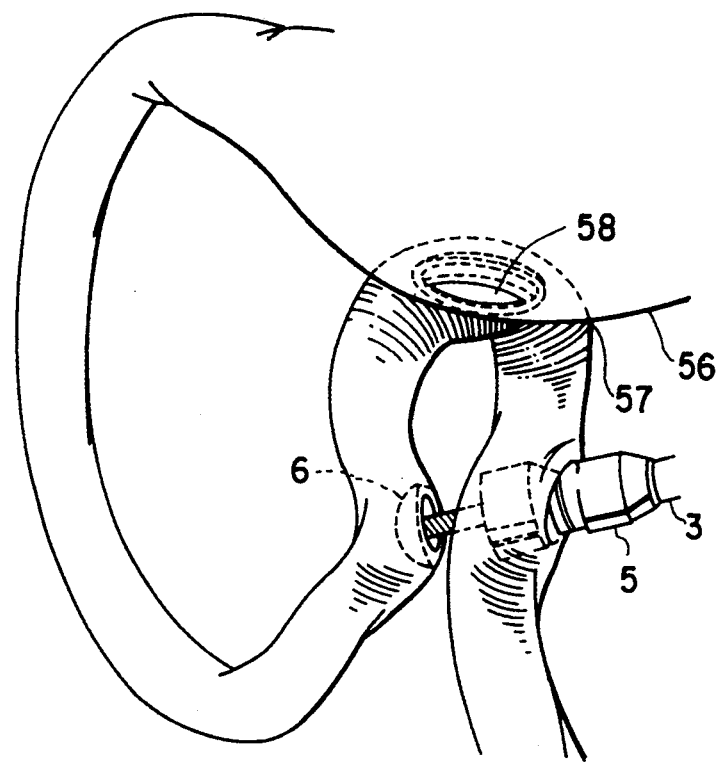
FIG. 4A is a perspective view, explaining the operation of stitching the walls of the stomach and duodenum together and forming an opening in the stitched parts of the walls, and the operation of stitching the walls of two portions of the duodenum together and cutting an opening in the stitched parts of the duodenum walls.
Figure 4B:
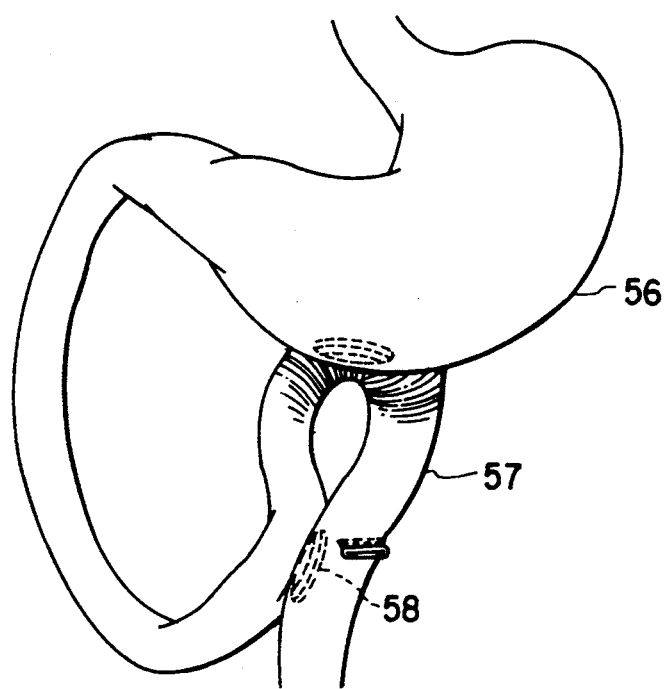
FIG. 4B is a perspective view of the stomach and the duodenum, illustrating the states these organs assume after the operations.

The stapler shown in FIGS. 1 and 2 can be used to perform operations other than stitching together the severed ends of two normal portions of the large intestine. The stapler can be employed to stitch the stomach wall and the duodenum wall together and, almost at the same time, form an opening in the stitched parts of the wall of these organs, as is shown in FIGS. 4A and 4B. Alternatively, it can be used to stitch together the walls of two portions of the duodenum and cut, almost at the same time, an opening in the stitched walls of the duodenum, as is illustrated in FIGS. 4A and 4B.

A surgical stapler according to a second embodiment of the present invention will be described with reference to FIGS. 5 and 6. The components identical or similar to those of the first embodiment are denoted by the same numerals in FIGS. 5 and 6 and will now be described in detail.

As can be understood from FIGS. 5 and 6, the stapler is characterized in two respects. First, a hollow cylinder 60 is located, surrounding the rigid tubular shaft 23. Second, two optical systems, i.e., an observation system 61 and an illumination system 62, are arranged within the hollow cylinder 60.

Located at the distal end of the staple applier 5 and, thus, opposing the anvil 6, both optical systems 61 and 62 provide a surgeon with a close-up image of the tissues clamped between the applier 5 and the anvil 6. This helps the surgeon to determine, more accurately, the state of the tissues which have just been stapled and severed.

Another surgical stapler according to a third embodiment of the present invention will be described with reference to FIGS. 7 and 8. The components identical or similar to those of the first embodiment are designated by the same numerals in FIGS. 7 and 8 and will now be described in detail.

As is shown in FIGS. 7 and 8, the third embodiment is characterized in two respects. First, a staple holder 63 is removably attached to the distal end of the rigid tubular shaft 23. Second, the anvil 6 is coupled to the distal end of the insertion section 2 and slidably mounted on the rigid tubular shaft 23.

The staple holder 63 has its front shaped like a rounded cone so that the holder 63 may smoothly be inserted into an organ. The stapler holder 63 has an annular groove in its back. Fitted in the annular groove is a ring-shaped staple-holding member 64. The staple-holding member 64 is designed to hold staples 35 such that the staples 35 are arranged in concentric two circles. The anvil 6 is a hollow cylinder which has an opening at the front and which can be moved back and forth, sliding along the rigid tubular shaft 23.

In operation, the anvil 6 and the stapler holder 63 are positioned, spaced apart, such that target tissues (not shown) are placed between them. Then, a hydraulic medium is pumped into the annular space 32 through the hydraulic tubes 26, raising the pressure in that space 32. The anvil body 65 slidably fitted in the anvil 6 and the cutter 38 connected to the anvil body 65 are thereby thrust forward. As a result, the tissues are clamped between the anvil body 65 and the back of the staple holder 63. As the anvil body 65 is further thrust forward, the legs 35a of each staple 35 held in the staple-holding member 64 will pierce the tissues, then abut on the bottom of one of two annular grooves 66 formed in the end face of the anvil body 65, and are finally bent toward each other. As a result of this, the staples 35 stitch the tissues together, forming two circular seams. At the same time, the cutter 38, moving forward along with the anvil body 65, excises those parts of the tissues which are inside the inner circular seam.

With the third embodiment it is possible to remove the staple holder 63 from the rigid tubular shaft 23 once the tissues have been stapled together. The staple holder 63, thus removed, can be replaced by a new one which will be used to staple other tissues and excise the unnecessary parts of the tissues.

A surgical stapler according to a fourth embodiment of this invention will be described in reference to FIGS. 9, 10, and 11.

The stapler 68 of this embodiment is designed for use in combination with an endoscope 67 having a forceps channel.

Figure 10:
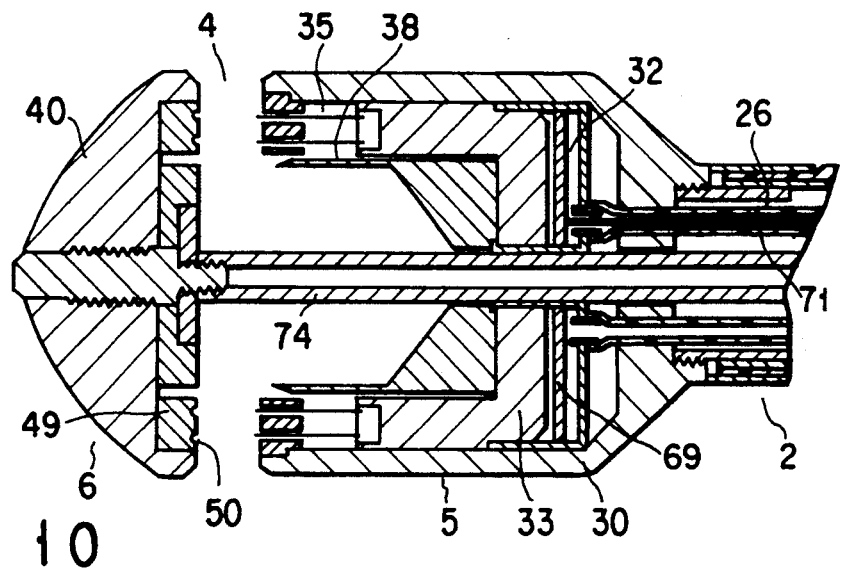
FIG. 10 is a sectional side view showing the stapling member of the stapler shown in FIG. 9.

As shown in FIG. 10, a pusher ring 69 is located at the back of the staple pusher 33. A pusher wire 71 extends through one of the hydraulic tubes 26 and is connected at its distal end to the pusher ring 69. The proximal end of the pusher wire 71 is fastened to a pusher/cutter driving member 73 which is set in sliding engagement with the operation section 72 of the stapler 68.

As in the first embodiment (FIG. 1), the stapling member 4 comprises a staple applier 5 and an anvil 6. The anvil 6 is connected to the distal end of a rigid tubular shaft 74. The proximal end of the rigid tubular shaft 74 is coupled to an operating ring 75 which is mounted on the operation section 72 and can be moved back and forth along the axis of the section 72. When the operating ring 75 is moved so, the anvil 6 is moved toward and away from the staple applier 5.

Figure 11:
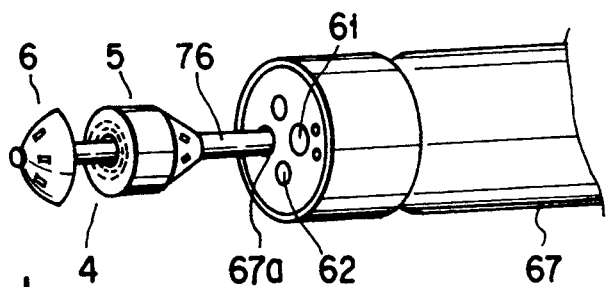
FIG. 11 is a perspective view of the stapling member of the stapler shown in FIG. 9.

As shown in FIG. 11, an insertion tube 76 is fastened to the proximal end of the housing 30 of the staple applier 5. The insertion tube 76 can be inserted into the forceps channel 67a of the endoscope 67. The insertion tube 76 contains various components, and the tube 76 and these components constitute an insertion section 77. The insertion section 77 is flexible and removably coupled to the operation section 72.

Assume the insertion section 77 is disconnected from the operation section 72. In this condition, the insertion section 77 can be inserted into the endoscope 67 through the open distal end of the forceps channel 67a until its proximal end portion protrudes from the cap 67b (FIG. 9) of the forceps channel 67a. The insertion section 77 can therefore be connected to the operation section 72. Hence, the stapler 68 can be used in combination with the endoscope 67.

As is shown in FIG. 11, the distal end of the endoscope 67 contains an observation optical system 61 and an illumination optical system 62.

Both the endoscope 67 and the stapler 68 are inserted in an organ. While seeing the interior of the organ through the endoscope 67, a surgeon operates the pusher/cutter driving member 73, pushing the pusher ring 69 forward. The pusher 33 and the cutter 38 are thereby thrust forward, stapling the target tissues of the organ and excising the unnecessary parts thereof.

Since the endoscope 67 can be inserted to a deep portion of the organ, allowing a surgeon to see the interior of the deep portion of the organ, the surgeon can move the stapling member 4 of the stapler 68 to a desired position in the organ. The surgeon can, therefore, stitch the target tissues together appropriately at that position, while looking at the image of the tissue through the endoscope 67.

Another stapler according to a fifth embodiment of the invention will be described with reference to FIGS. 12, 13, and 14. This embodiment is designed to apply staples to tissues, forming straight parallel seams, thereby stitching the tissues together.

Figure 12:
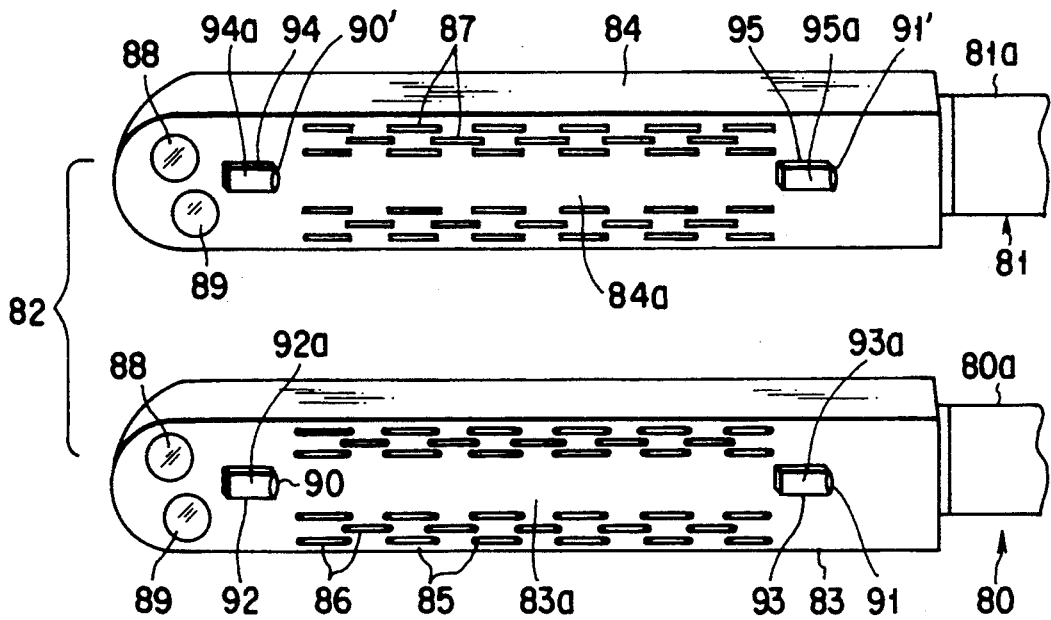
FIG. 12 is a perspective view illustrating the stapling member of a surgical stapler according to a fifth embodiment of the present invention.
Figure 13:
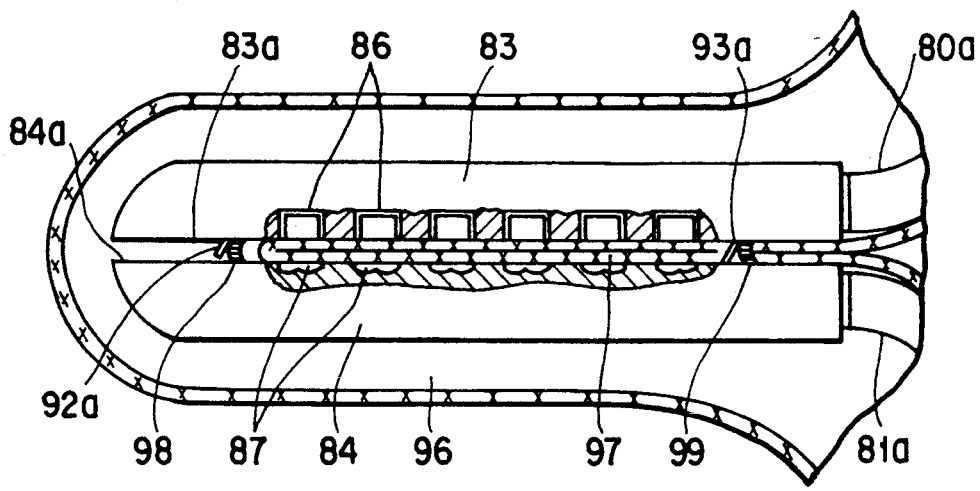
FIG. 13 is a cutaway side view showing the cartridge and anvil of the stapling member of FIG. 12, clamping the walls of a tubular organ.

As shown in FIG. 12, this stapler has two insertion sections 80 and 81. The first insertion section 80 has a bendable portion 80a. Similarly, the second insertion section 81 has a bendable portion 81a. A cartridge 83 is coupled to the bendable portion 80a of the first insertion section 80. An anvil 84 is connected to the bendable portion 81a of the second insertion section 81.

The cartridge 83 and the anvil 84 constitute a stapling member 82. The cartridge 83 and the anvil 84 are substantially identical in size and shape; they have flat surfaces 83a and 84a, respectively. The surfaces 83a and 84a contact each other when the cartridge 83 and the anvil 84 are positioned in mutual alignment.

The cartridge 83 has a plurality of slits 85 formed in the surface 83a and arranged in six rows—three on one side of the center line, and the remaining three on the other side of the center line. Loosely fitted in these slits 85 are staples 86 which can be driven from the surface 83a by means of a staple pusher (not shown).

The anvil 84 has a plurality of grooves 87 formed in the surface 84a and arranged in six rows—three on one side of the center line, and the remaining three on the other side of the center line. The grooves 87 are so positioned as to meet the corresponding slits when the anvil 84 is connected to and aligned with the cartridge 83. Hence, when each staple 86 is driven from the cartridge 84, its legs abut on the bottom of the groove 87 and are eventually bent toward each other.

The cartridge 83 has an illumination window 88 and an observation window 89 formed in the flat surface 83a and located side by side. Similarly, the anvil 84 has an illumination window 88 and an observation window 89 formed in the flat surface 83a and located side by side.

Each illumination window 88 is optically connected to a light-guiding fiber (not shown), and each observation window 89 is optically coupled to an image-transmitting fiber (not shown). The fibers connected to the windows 88 and 89 formed in the surface 83a extend through the cartridge 83 and the first insertion section 80 and are coupled to the operation section (not shown) of the stapler. The fibers connected to the windows 88 and 89 formed in the surface 84a extend through the anvil 84 and the second insertion section 81 and are coupled to the operation section. The stapling member 82 therefore has an optical system comprised of the windows 88 and 89, the light-guiding fibers, and the image-transmitting fibers.

The cartridge 83 has two forceps channels 90 and 91 opening at the flat surface 93a and communicate with the operation section via the first insertion section 80. The anvil 84 has two forceps channels 90' and 91' opening at the flat surface 94a and communicate with the operation section via the second insertion section 81. The cartridge 83 has two forceps-guiding grooves 92 and 93 formed in the surface 83a, located at the distal and proximal end portions of the cartridge 83, respectively, and communicating with the forceps channels 90 and 91, respectively. Similarly, the anvil 84 has two forceps-guiding grooves 94 and 95 formed in the surface 84a, located at the distal and proximal end portions of the anvil 84, respectively, and communicating with the forceps channels 90' and 91', respectively. The cartridge 93 contains two forceps guides 92a and 93a, respectively, for directing forceps from the flat surface 83a. Also, the anvil 84 has two forceps guides 94a and 95a protruding from the rims of the forceps-guiding grooves 94 and 95, respectively, for guiding forceps from the flat surface 84a in the direction perpendicular thereto.

The stapler shown in FIG. 12 is operated in the following way to staple the walls of a tubular organ together. First, as shown in FIG. 13, the cartridge 83 and the anvil 84, which are coupled to the bendable portions 80a and 81a of the insertion sections 80 and 81, respectively, are inserted through the mouth into a tubular organ 96 such as the duodenum and moved to a desired portion in the organ 96. The operation section (not shown) is operated, bending the bendable portions 80a and 81a of the insertion sections 80 and 81, thereby aligning the cartridge 83 and the anvil 84 and clamping the walls 97 of the tubular organ 96 between the flat surfaces 83a and 84a.

Then, guide wires 98 and 99, which are fastened at their proximal end to the operation section, are inserted into the forceps channels 90 and 91 of the cartridge 83 through the first insertion section 80, until their distal end portions project from the forceps-guiding grooves 92 and 93, respectively. The forceps guide 92a and 93a guides the distal ends of the guide wires 98 and 99 into the forceps-guiding grooves 94 and 95 of the anvil 84.

Next, two forceps (not shown) are inserted into the forceps channels 90' and 91' of the anvil 84 through the second insertion section 81, until their distal ends protrude into the forceps-guiding grooves 94 and 95. The forceps are manipulated, taking hold of the distal ends of the guide wires 98 and 99. The forceps are pulled, first from the channels 90' and 91' and then from the second insertion section 81, until the guide wires 98 and 99 reach the operation section fastened to the proximal end of the second insertion section 81. Both wires 98 and 99 are tied to the operation section. As a result, the cartridge 83 and the anvil 84 are connected together.

After the cartridge 83 and the anvil 84 have been thus connected together, the staple pusher (not shown) is thrust forward, applying the staples 86 from the cartridge 83 to the walls 97 of the organ 96 clamped between the flat surfaces 83a and 84a. The legs of each staple 86 pierce through the walls 97, and the bottom of the groove 87; and they are eventually bent toward each other. As a result, the staples 86 stitch the walls 97 together, forming six seams.

After the walls 97 have been thus stapled, the guide wires 98 and 99 are slackened, whereby the cartridge 83 and the anvil 84 are spaced apart, releasing the stapled walls 97. At this time, the illumination windows 88 and the observation windows 89 leave the walls 97, enabling the surgeon to see the state the stapled walls 97 assume.

Either the cartridge 83 or the anvil 84 may have an excision means for excising the unnecessary parts of the stapled walls 97 of the tubular organ 96. The guide wires 98 and 99 may be fastened by caps which are secured with silicon used to inject a contrast medium into a drainage tube.

Figure 14:
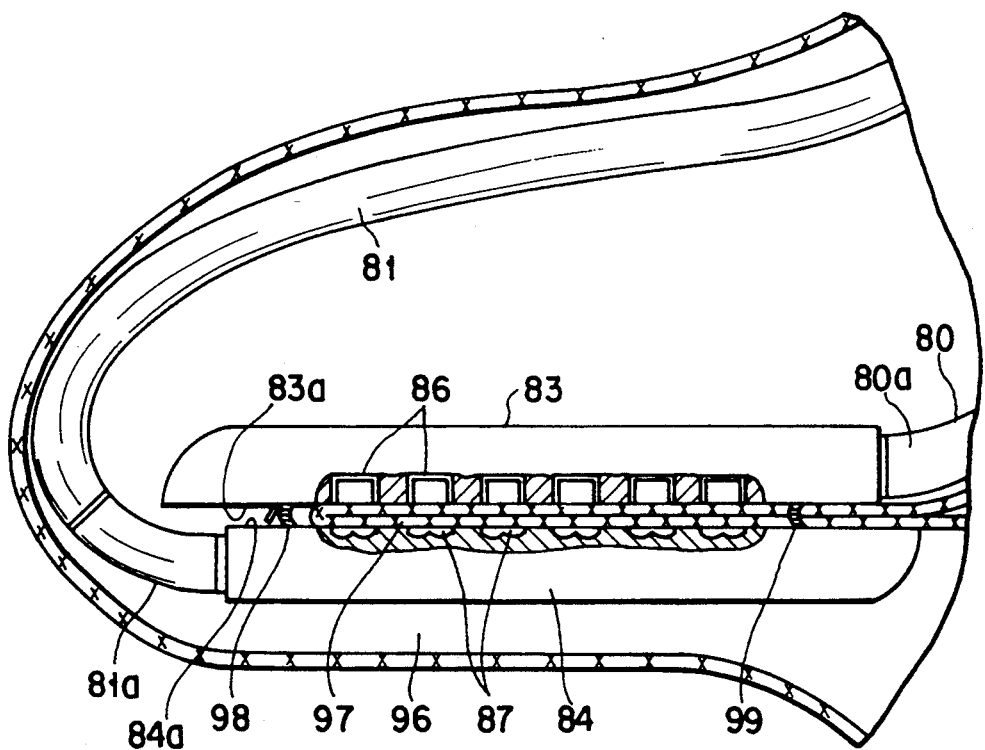
FIG. 14 is a cutaway side view showing the cartridge and anvil of the stapling member of FIG. 12, positioned in a different way and clamping the walls of a tubular organ.

The anvil 84 may be positioned with its distal and proximal ends aligned with the proximal and distal ends of the cartridge 83, as is illustrated in FIG. 14, by operating the operation section and by subsequently bending the bendable portions 80a and 81a of the insertion sections 80 and 81. In this case, too, the walls 97 of the tubular organ 96 are clamped between the cartridge 83 and the anvil 84. In this condition, the staples 86 may be applied, thereby to stitch the organ walls 97 together.

Since the cartridge 83 and the anvil 84 have illumination and observation means each, the surgeon can see and check the state the walls 97 assume immediately after they have been stapled. Not permanently connected, the cartridge 83 and the anvil 84 can be independently inserted into an organ, moved to any desired position therein, and positioned—independently of each other. Hence it is easy for the surgeon to guide them to the target tissues. In addition, no opening needs to be made in the organ to allow the insertion of the stapling member 82 into the organ since the member 82 can be inserted through the mouth. This serves to reduce the patient's suffering and discomfort.

Figure 17:
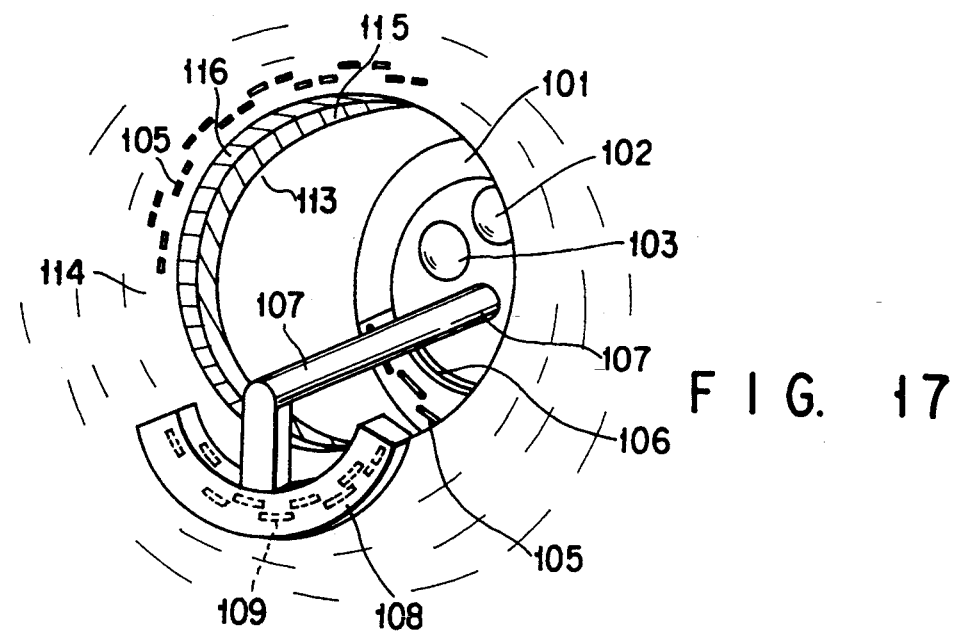
FIG. 17 is a perspective view of the distal end portion of the stapler/endoscope, explaining how the stapler is manipulated to clamp the wall of the stomach and that of the duodenum between the anvil and staple holder of the stapler.

A stapler/endoscope of direct-view type, which is a sixth embodiment of the invention, will be described with reference to FIGS. 15, 16, and 17.

As is evident from FIG. 15, the stapler/endoscope comprises a flexible insertion section 100. The insertion section 100 has a bendable portion 100a. Coupled to the bendable portion 100a is a hollow cylindrical housing 101 which has an observation window 102 and an illumination window 103 formed in its distal-end face. The stapler/endoscope further comprises an operation section (not shown) which is connected to the proximal end of the insertion section 100. The operation section has a lever (not shown), which can be operated to bend the bendable portion 100a of the insertion section 100.

A staple holder 104 is secured to the distal-end face of the housing 101. The stapler holder 104 is an arcuate member, extending for about one third of the circumference of the housing 101. A plurality of staples 105 are held in the holder 104, arranged in two concentric arcuate rows. An arcuate cutter 106 is located inside the staple holder 104 and coaxial with the housing 101, and can be moved to project, when necessary, from the distal-end face of the housing 101.

An anvil shaft 107 extends through the housing 101 and projects from the distal-end face thereof. The shaft 107 can be moved back and forth along the axis of the hollow cylindrical housing 101. An anvil 108 is connected to the distal end of the anvil shaft 107. The anvil 108 opposes the staple holder 104 and is substantially identical to the staple holder 104 in shape and size. It has grooves 109 formed in the surface facing the staple holder 104 and arranged in two rows. The grooves 109 are so positioned as to receive the staples 105 held by the holder 104 when the shaft 107 is pulled backward, bringing the anvil 108 into contact with the staple holder 104.

The anvil shaft 107 can be moved back and forth as the operating knob (not shown) mounted on the operation section is operated, as in the first embodiment illustrated in FIGS. 1 and 2. The gap between the staple holder 104 and the anvil 108 is thereby adjusted. The housing contains a staple pusher (not shown), which can be driven back and forth along with the cutter 106 by operating the pusher/cutter driving lever which is rotatably connected to the operation section as in the first embodiment (FIGS. 1 and 2). Hence, when the operating knob is rotated, thrusting the shaft 107 backward, the anvil 108 is driven toward the housing 101. As a result, the body tissues placed between the staple holder 104 and the anvil 108 are clamped. Then, the pusher/cutter driving lever is squeezed, thrusting the staple pusher and the cutter 106 forward, whereby the staples 105 and the cutter 106 are pushed forward. The legs of each staple 105 pierce the tissues, abut on the bottom of the groove 109, are bent toward each other, thus fastening the tissues together. At the same time, the cutter 106 excises the unnecessary parts of the clamped tissues.

The stapler/endoscope of direct-view type, described above, is operated in the following way. As shown in FIG. 16, a part 112 of the duodenum 111 is stitched to the stomach 110 by using a laparoscope or by forming an opening in the abdominal wall. Next, an endoscope (not shown) having a forceps channel is inserted into the stomach 110 through the mouth. A cutter (not shown) is inserted into the stomach 110 through the forceps channel and manipulated, thereby forming two incisions 115 and 116 in the stomach wall and the duodenum wall. The stomach 110 and the duodenum 111 thereby communicate with each other. Then, the endoscope is pulled out.

Thereafter, the insertion section 100 of the stapler/endoscope is inserted into the stomach 110 through the mouth. The anvil 108 is moved into the duodenum 111 through the incisions 115 and 116 and so positioned as to oppose that portion of the duodenum wall 114 which is to be fastened to the stomach 110 as shown in FIG. 17. This done, the operating knob is rotated, moving the anvil 108 toward the staple holder 104 until the anvil 108 and the holder 104 clamp the wall 113 of the stomach 110 and duodenum 110 together.

Next, the pusher/cutter driving lever is squeezed, thereby driving the staples 105 from the staple holder 104 into the stomach wall 113 and the duodenum wall 114. The legs of each staple 105 pierce the tissues, abut on the bottom of the groove 109, are bent toward each other, thus fastening the walls 113 and 114 together. Simultaneously, the cutter 106 is thrust forward, cutting off those parts of the walls 113 and 114 which are inside the seams formed of the staples 105.

The sequence of operations, described in the preceding two paragraphs, is repeated several times, sewing the walls 113 and 114, all around the incisions 115 and 116.

Figure 18:
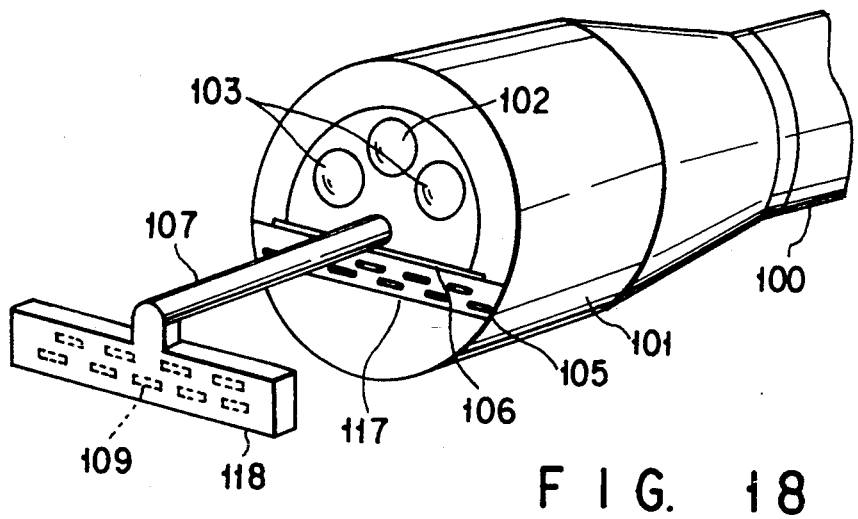
FIG. 18 is a perspective view of the distal end portion of a modification of the stapler/endoscope shown in FIG. 16.

FIG. 18 illustrates a modification of the stapler/endoscope shown in FIG. 16. The modified stapler/endoscope is characterized in that both the staple holder 117 and the anvil 118 are straight, not arcuate. The modified stapler/endoscope is manipulated in the same way as the stapler/endoscope shown in FIG. 16.

Both stapler/endoscope, shown in FIGS. 16 and 18, is advantageous in two respects. First, the anvil 108 or 118 is small enough to pass through a small incision made in an organ wall. Second, even if those portions of the organ walls which are to be stapled are relatively large, the surgeon can stitch them together and excise their unnecessary parts, while observing the portions of the organ walls.

A stapler/endoscope, which is a seventh embodiment of the invention, will be described with reference to FIGS. 19 to 21. This device comprises a staple-applying unit and an anvil forceps 128 which are structurally independent.

Figure 19:
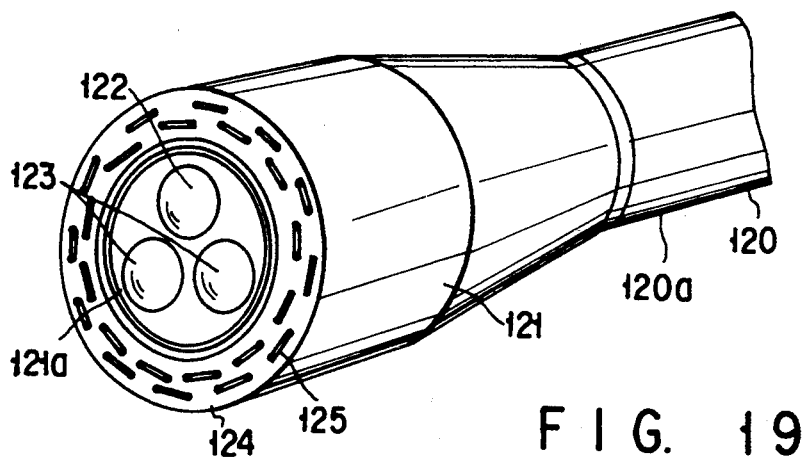
FIG. 19 is a perspective view of the distal end portion of a stapler/endoscope according to a seventh embodiment of this invention.

As shown in FIG. 19, the staple-applying unit comprises a flexible insertion section 120 and a housing 121 connected to the bendable portion 120a of the insertion section 120. The housing 121 contains a guide 121a which can project from the distal end of the housing 121. The guide 121a has an observation window 122 and two illumination windows 123 formed in its front end. An annular staple holder 124 is mounted on the distal-end face of the housing 121. The holder 124 holds a plurality of staples 125 arranged in two concentric circles.

Though not shown, the staple-applying unit comprises an operation section coupled to the proximal end of the insertion section 120. The operation section has an operating knob and a pusher/cutter driving lever (either not shown). The knob is rotated to bend the bendable portion 120a, and the lever is operated to move the guide 121a back and forth. As is shown in FIG. 21, the guide 121a has a ring 126 mounted on its circumference. The ring 126 has a projection 127 extending parallel to the axis of the guide 121a.

Figure 20:
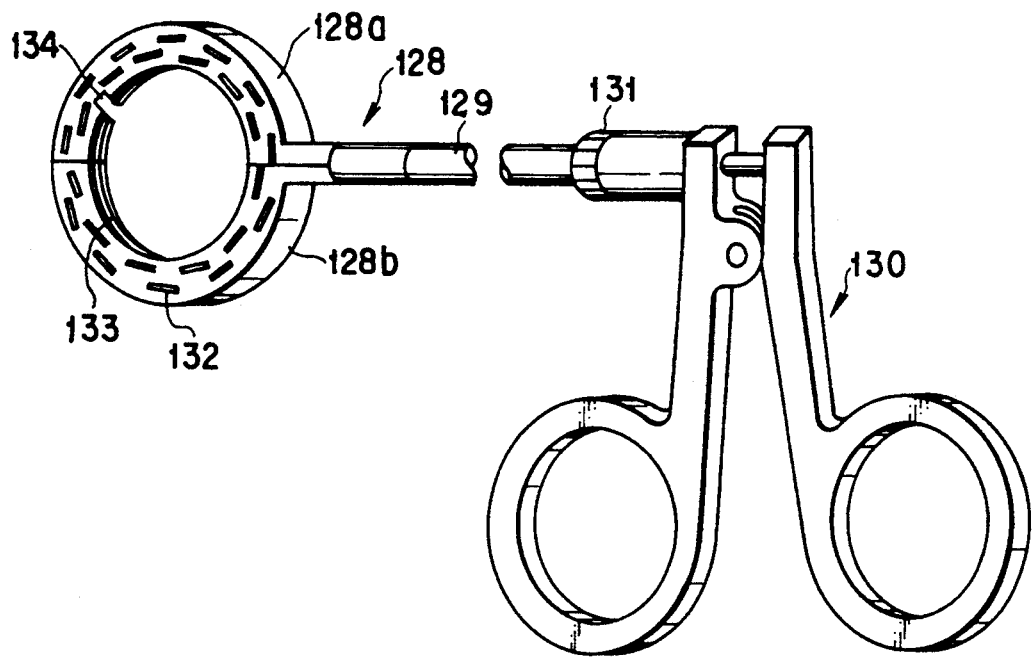
FIG. 20 is a perspective view of the anvil forceps used in the stapler/endoscope shown in FIG. 19.

FIG. 20 shows the anvil forceps 128. The anvil forceps 128 comprises two arcuate anvil halves 128a and 128b, an insertion section 129, a pair of handles 130, and a ring 131. Both anvil halves 128a and 128b are coupled to the distal end of the insertion section 129, and can rotate to move between their open and closed positions. The first handle 130 is fixed to the proximal end of the section 129, and the second handle 130 is rotatably coupled to the first handle 130. When the second handle 130 is rotated, the anvil halves 128a and 128b will be moved to their open position or their closed position. The ring 131 is rotatably mounted on the insertion section 129. When the ring 131 is rotated, the insertion section 129 will be rotated around its axis.

Each anvil half has a plurality of grooves 132 formed in its one side and arranged in two arcs. These grooves 132 will oppose the staples 125 held in the staple holder 124 when the anvil halves 128a and 128b are mounted on the guide 121a of the insertion section 120. Further, each anvil half has an arcuate groove 133 in its inner circumference. The arcuate grooves 133 of the anvil halves 128a and 128b will form a complete annular groove when the halves 128a and 128b are placed in their closed positions. The first anvil half 128a has a straight groove 134 for positioning the half 128a when the half 128a is mounted on the guide 121a.

Figure 21:
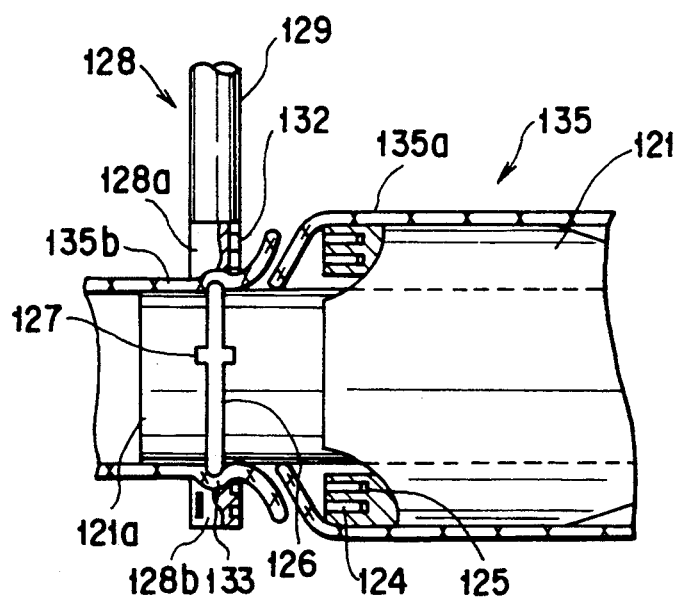
FIG. 21 is a sectional side view, explaining how the stapler is operated.

With reference to FIG. 21 it will be described how the stapler/endoscope shown in FIGS. 19 and 20 is used to staple together the severed two portions of, for example, the large intestine 135 after a diseased portion of the intestine 135 has been cut and removed.

First, the staple-applying unit is inserted into the large intestine 135 through the anus. Meanwhile, the anvil forceps 128 is inserted into the abdominal cavity through an incision cut in the abdominal wall. The staple-applying unit is further inserted until the housing 121 reaches the severed edge 135a of the intestine 135. At this position, the staple holder 124 is covered with the severed edge 135a as is shown in FIG. 21. The anvil forceps 128 is manipulated, placing its anvil halves 128a and 128b around the other severed edge 135b of the intestine 135. Further, the severed edge 135b of the intestine 135 is moved to the other severed edge 135a by means of a holding forceps (not shown), until its severed edge abuts on the severed edge 135a of the intestine 135 as is illustrated in FIG. 21.

Then, the guide 121a is thrust forward into the edge 135b of the large intestine 135. Next, the anvil halves 128a and 128b are rotated to their closed positions and moved along and around their axes until the ring 126 and projection 127 mounted on the guide 121a fit into the arcuate grooves 133 and the straight groove 134. As a result, the anvil forceps 128 clamps and holds the severed edge 135b of the intestine 135 on the guide 121a.

In this condition, the staples 125 are driven from the staple holder 124 into the overlapping severed edges 135a and 135b of the large intestine 135. As a result, the legs of each staple 125 pierce the edges 135a and 135b, abut on the bottom of the groove 132 of the anvil 128, are bent toward each other, thus stapling the severed edges 135a and 135b together.

With the stapler/endoscope shown in FIGS. 19 and 20 it is unnecessary to squeeze the severed edge 135a by stitching the edge 135a with a tying thread and subsequently pulling the thread to squeeze the severed edge 135a. Further, the anvil forceps 128 is easy to insert into a body cavity, which helps to shorten the time required to stitch together the severed edges of a tubular organ. In addition, the surgeon can see the stapled edges of the intestine 135 through the observation window 122, and can thereby examine the state of the edges 135a and 135b which have just been stapled together.

Figure 23:
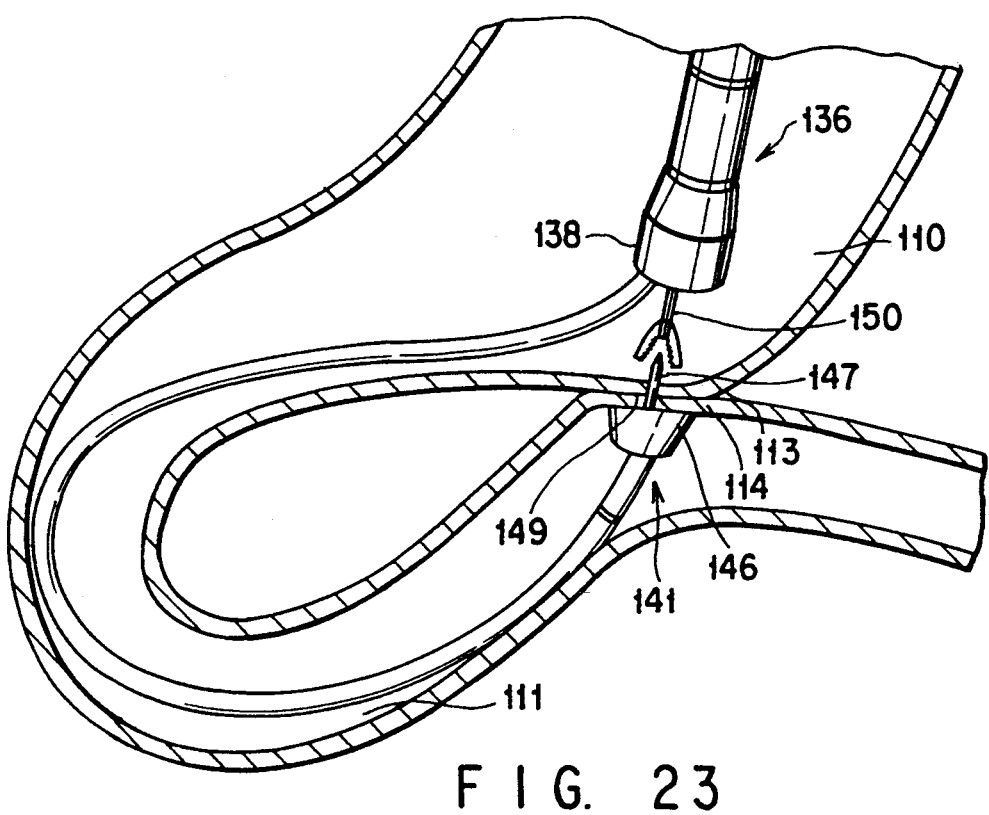
FIG. 23 is a diagram explaining how the auxiliary unit of the tandem stapler/endoscope is inserted into the duodenum and guided to a diseased portion thereof.
Figure 24:
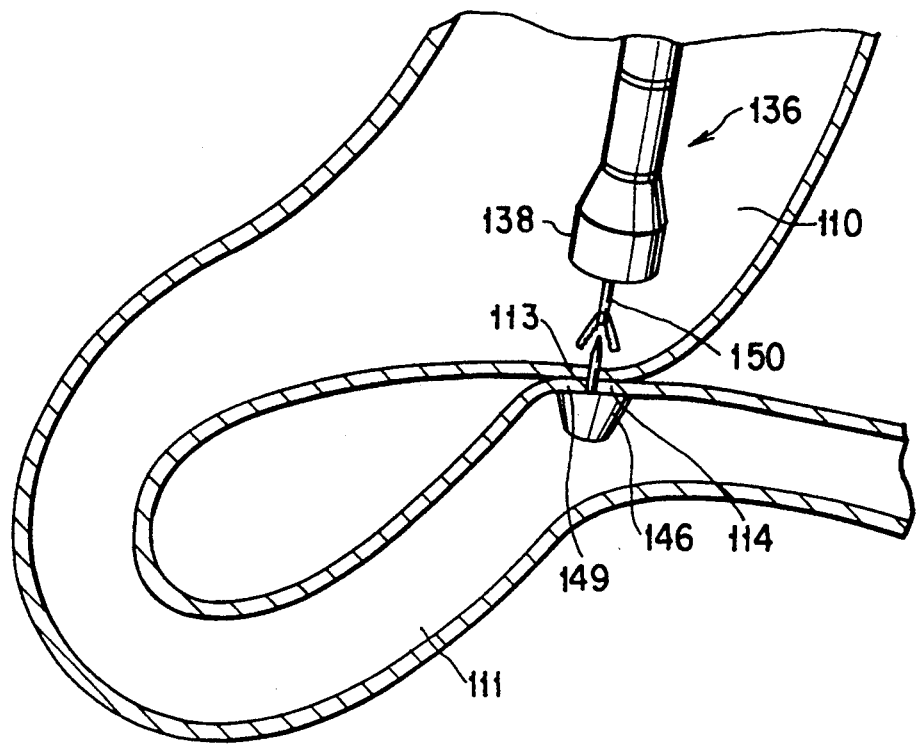
FIG. 24 is a diagram explaining how the anvil, which is a part of the auxiliary unit, is left on the diseased portion of the duodenum.

A tandem stapler/endoscope, which is an eighth embodiment of this invention, will be described with reference to FIGS. 22, 23, and 24.

Figure 22:
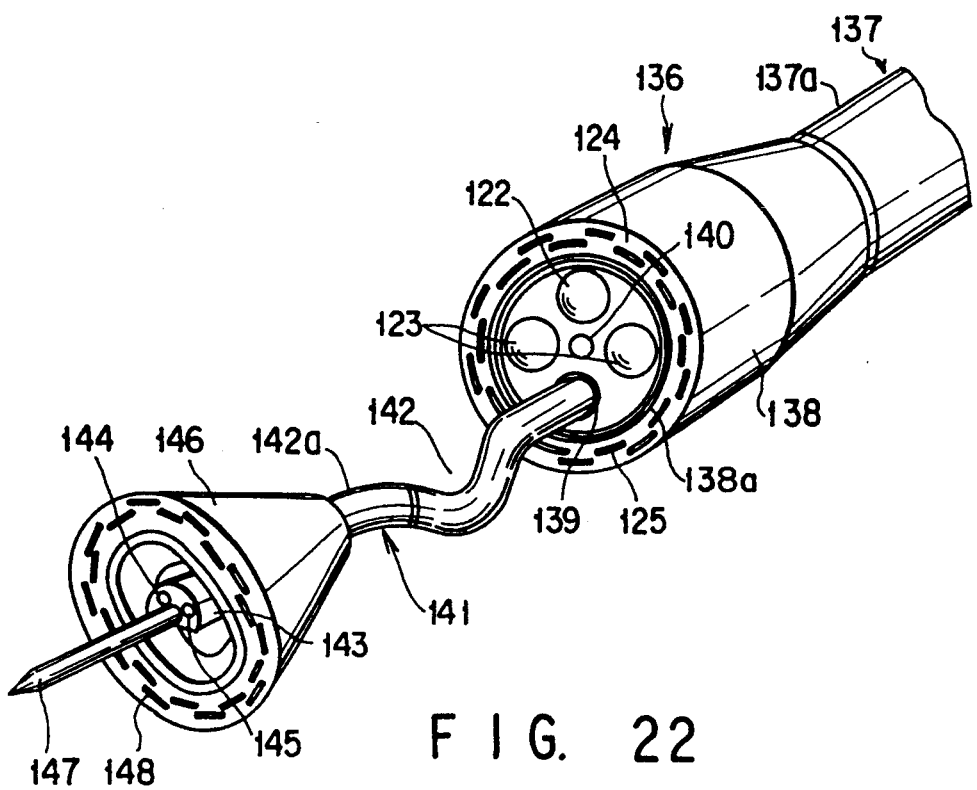
FIG. 22 is a perspective view of the distal end portion of a tandem stapler/endoscope which is an eighth embodiment of this invention.

As FIG. 22 shows, the stapler/endoscope comprises a main unit 136 and an auxiliary unit 141. The main unit 136 comprises a flexible insertion section 137 and a housing 138 connected to the bendable portion 137a of the insertion section 137. The housing 138 has a hole 140 made in its distal-end face and positioned coaxial with the axis of the insertion section 137. The housing 138 also has an observation window 122, two illumination windows 123, and a channel 139—all formed in the distal-end face and arranged around the hole 140. The housing 138 has an annular staple holder 124 on its distal-end face. Held in the holder 124 is a plurality of staples 125 arranged in two concentric circles. The housing 138 contains an annular cutter 138a which can be moved back and forth, sliding through the annular staple holder 124.

The auxiliary unit 141 comprises a flexible insertion section 142, a distal end portion 143, an anvil 146, and an anvil shaft 147. The insertion section 142 has a bendable portion 142a. The section 142 has its proximal end inserted in the channel 139 of the main unit 136. The anvil 146 is removably connected to the distal end portion 143 of the insertion section 142, which distal end portion 143 has an observation window 144 and an illumination window 145 formed in its front-end face. The anvil 146 has the anvil shaft 147 which can be inserted into the hole 140 made in the distal-end face of the housing 138. The anvil 146 has a plurality of grooves 148 formed in its front-end face. The grooves 148 are arranged in two concentric circles and so positioned as to receive the staples 125 held in the staple holder 124 when the anvil 146 abuts on the housing 138 of the main unit 136, with the anvil shaft 147 inserted in the hole 140.

It will be described how the tandem stapler/endoscope is operated to stitch a part of the duodenum 111 to the stomach 110 and form an opening in the stitched parts of the walls of these organs.

First, the main unit 136 is inserted into the stomach 110 through the mouth. Then, the auxiliary unit 141 extending from the main unit 136 is inserted into the duodenum 111 as is shown in FIG. 23. The auxiliary unit 141 is manipulated until it abuts on the diseased portion 114 of the duodenum 111, when the anvil shaft 147 pierces the diseased portion 114 of the duodenum 111 and the wall 113 of the stomach 110. Then, the insertion section 142 is pulled and disconnected from the anvil 146, leaving the anvil 146 on the walls 113 and 114 of the stomach 110 and duodenum 111, as is illustrated in FIG. 24.

Thereafter, the housing 138 of the main unit 136 moves to a position near the tip of the anvil shaft 146 protruding into the stomach 110. A holding forceps 150 is inserted into the stomach 110 through the hole 140 of the housing 138. The forceps 150 is manipulated, holding the tip of the anvil shaft 147, and then pulled backward, thereby drawing the anvil shaft 147 into the hole 140.

The walls 113 and 114 of the organs 110 and 111 are thereby clamped between the housing 138 and the anvil 146. Next, the staples 125 are driven into the clamped walls 113 and 114 in the same manner as in the embodiments described above. The legs of each staple 125 pierce the walls 113 and 114, abut on the bottom of the groove 148 of the anvil 146, are bent toward each other, thus stapling the clamped walls 113 and 114 and forming two circular seams on these walls. As a result, the duodenum 111 is fastened to the stomach 110. At the same time the walls 113 and 114 are stapled together, the annular cutter 138a is thrust forward, excising those parts of the walls 113 and 114 which are located inside the circular seams.

With the tandem stapler/endoscope, too, it is possible for the surgeon to observe the state the walls 113 and 114 assume immediately after they have been stapled together. The tandem stapler/endoscope is advantageous in another respect. No opening needs to be made in an organ to allow the insertion of the units 136 and 146 into the organ since they can be inserted through the mouth. This serves to reduce the patient's suffering and discomfort.

Figure 25:
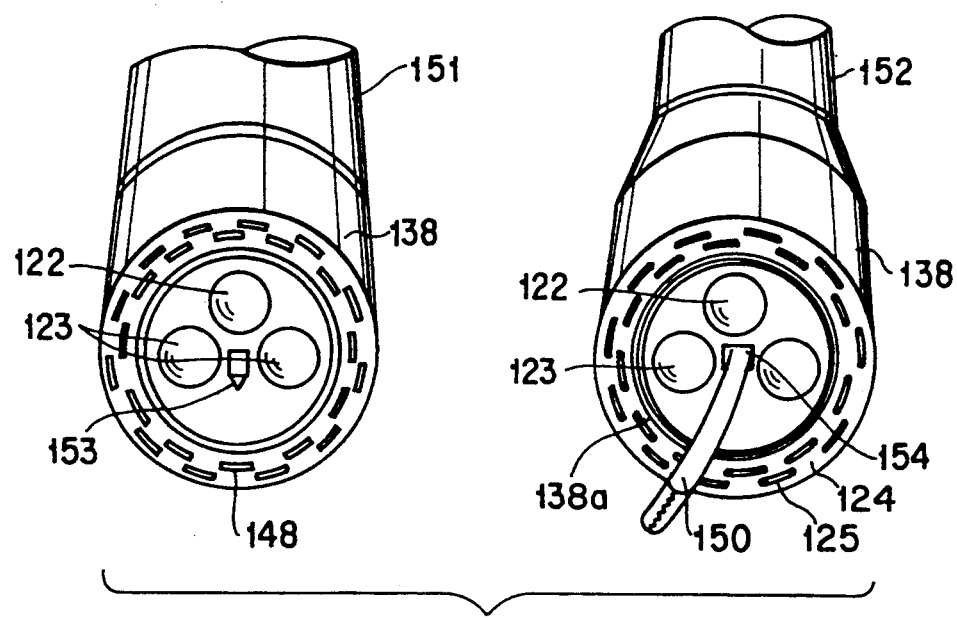
FIG. 25 is a perspective view showing the main and auxiliary units of a tandem stapler/endoscope according to a ninth embodiment of the invention.

Another tandem stapler/endoscope, which is a ninth embodiment of the present invention, will be described with reference to FIGS. 25, 26, and 27. This device comprises two units 151 and 152 which are basically identical to the main unit 136 of the eighth embodiment (FIG. 22). Hence, the components identical to those of the eighth embodiment will be denoted by the same numerals and will now be described in detail.

The housing 138 of the first unit 151 has a plurality of grooves 148 formed in its front-end face and arranged in two concentric circles. An anvil shaft 153 protrudes from the front-end face of the housing 138. The anvil shaft 153 has a square cross section and a tip shaped like a pyramid.

The housing 138 of the second unit 152 has an annular staple holder 124 on its distal-end face. Held in the holder 124 is a plurality of staples 125 arranged in two concentric circles. A square hole 154 is made in the front-end face of the housing 138 for receiving the anvil shaft 153 of the first unit 151. A holding forceps 150 extends through the hole 154, protruding from the front-end face of the housing 138. The housing 138 contains an annular cutter 138a which can be moved back and forth.

Figure 26:
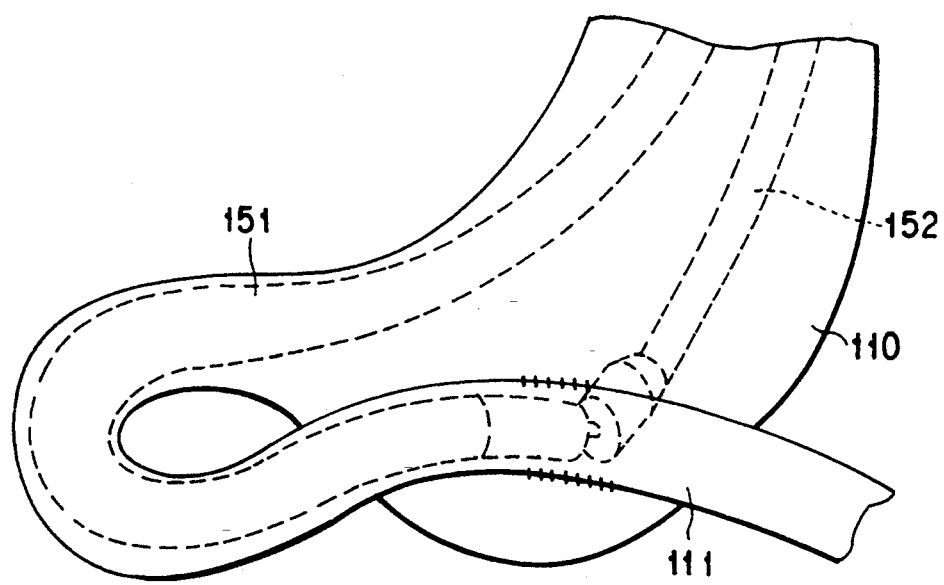
FIG. 26 is a diagram explaining how the first unit of the tandem stapler/endoscope shown in FIG. 25 is inserted into the duodenum and guided to a diseased portion thereof.
Figure 27:
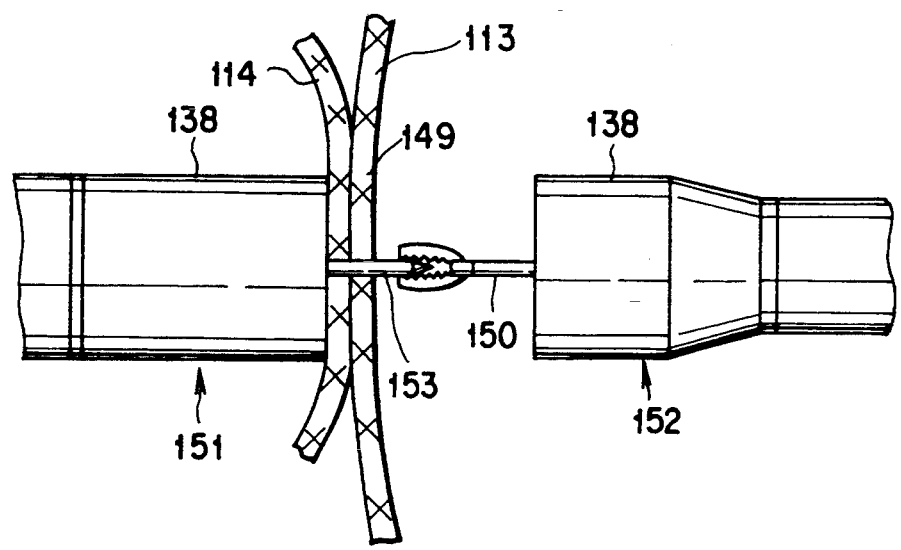
FIG. 27 is a side view of the first and second units of the tandem stapler/endoscope shown in FIG. 25.

The first unit 151 and the second unit 152 are inserted through the mouth into the duodenum 111 and the stomach 110, respectively, as is illustrated in FIG. 26. The first unit 151 is made to abut on a diseased portion 114 of the duodenum 111, when the anvil shaft 153 pierces the wall 114 of the duodenum 111. The holding forceps 150 is manipulated, taking hold on the anvil shaft 153. Then the forceps 150 is pulled into the housing 138 of the second unit 152, drawing the anvil shaft 153 into the hole 154 as is shown in FIG. 27. As a result, the first unit 151 abut on the second unit 152 and is aligned coaxial therewith, clamping the wall 114 of the duodenum 111 and the wall 113 of the stomach 110 between them. At the same time, the grooves 148 oppose the staples 125 held in the stapler holder 124.

Thereafter, the staples 125 are applied in the same manner as in the eighth embodiment, stapling the clamped walls 113 and 114. Simultaneously, the annular cutter 138a is thrust forward, excising those parts of the walls 113 and 114 which are located inside the circular seams formed of the staples 125. Hence, the tandem stapler/endoscope achieves the same advantage as the eighth embodiment (FIG. 23).

A stapler/endoscope 155 according to a tenth embodiment of this invention will be described with reference to FIGS. 28 to 31. The device 155 is similar to the main unit 136 of the eighth embodiment (FIG. 22). Therefore, the components identical to those of the eighth embodiment will be denoted by the same numerals and will now be described in detail.

As is shown in FIG. 30, the housing 138 of the stapler/endoscope 155 has a screw hole 157 which extends along the axis of the housing 138 and which communicates with a channel 156. The screwed proximal end portion 159 of an anvil shaft 158 is inserted in the screw hole 157, whereby the anvil shaft 158 is connected to the housing 138. The anvil shaft 158 is coupled by an anvil wire 160 to an anvil-rotating knob 162 mounted on an operation section 161. As shown in FIG. 28, a helical anvil 153 is secured to the distal end of the anvil shaft 158. The anvil 163 has a sharp tip 164. As shown in FIG. 29, the anvil 163 has a plurality of grooves 148 formed in its back.

The stapler/endoscope 155 is operated in the following way. As shown in FIGS. 30 and 31, the wall 114 of the duodenum 111 is stitched to the wall 113 of the stomach 110 by using a laparoscope or by forming an opening in the abdominal wall. Thereafter, the stapler-/endoscope 155 is inserted into the stomach 110 through the mouth, until the anvil 163 is pressed onto the wall 113 of the stomach 110. Then, the anvil-rotating knob 162 is rotated, thereby rotating the anvil shaft. Since the distal end portion 158 of the shaft 158 is in screw engagement with the screw hole 157, the anvil shaft 158 is thrust forward, while rotating the anvil 163. The anvil 163 therefore pierces the wall 113 of the stomach 110, then pierces the wall 114 of the duodenum 111, and finally penetrates into the duodenum 111.

Next, the anvil-rotating knob 162 is rotated in the opposite direction, rotating the anvil shaft 158 in that direction. The anvil shaft 158 is therefore pulled backward, while rotating the anvil 163. The anvil 163 therefore pulls the wall 114 of the duodenum 111 to the wall 113 of the stomach 110, whereby the walls 113 and 114 are clamped between the housing 138 and the anvil 163. At this time, the pusher/cutter driving lever 8 rotatably coupled to the operation section 161 is squeezed, driving staples 125 into the walls 113 and 114 from the staple holder 124. The legs of each staple 125 pierce the walls 113 and 114, abut on the bottom of the groove 148 of the anvil 163, are bent toward each other, thus stapling the clamped walls 113 and 114.

Figure 34:
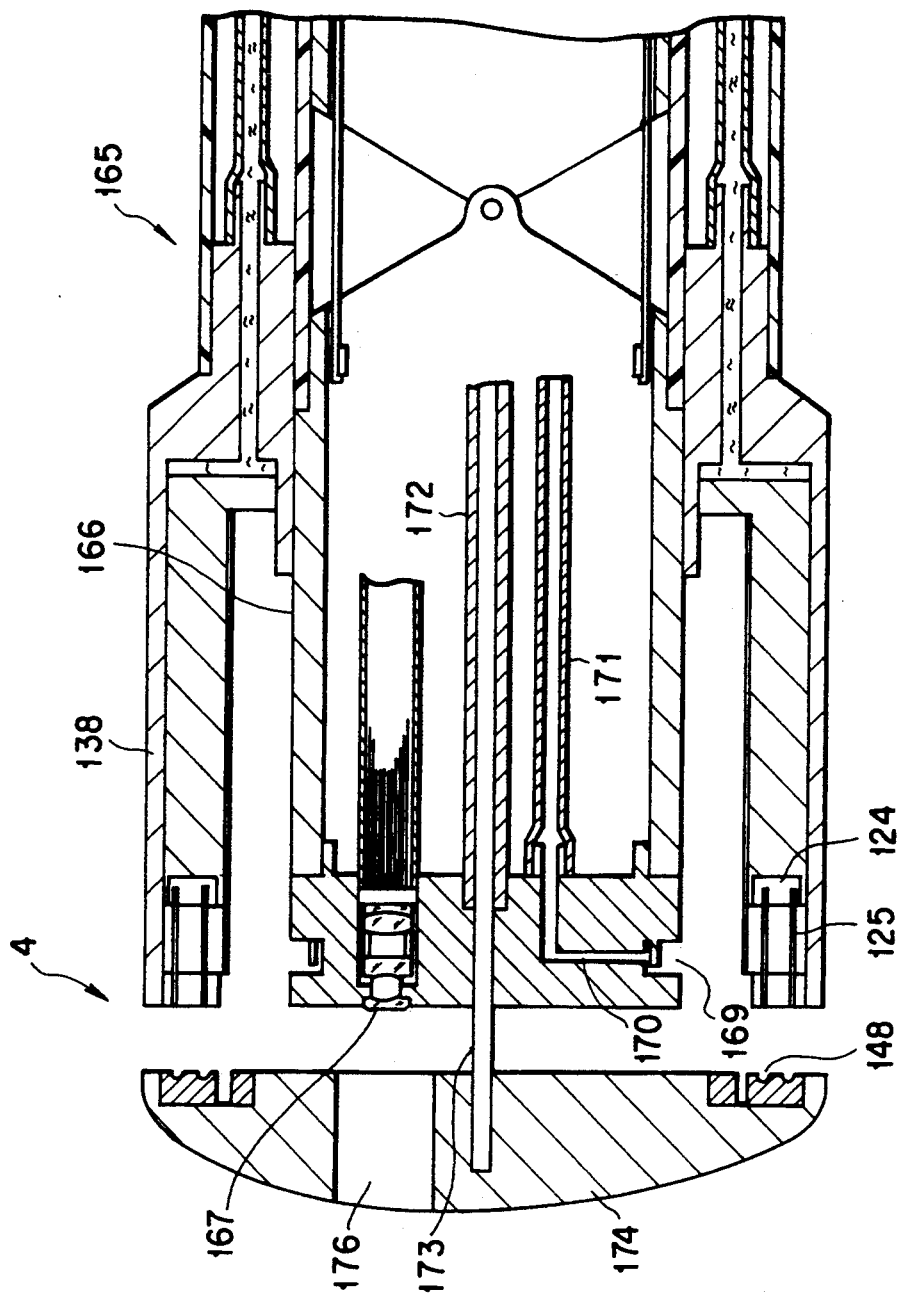
FIG. 34 is a sectional side view illustrating the distal end portion of the stapler/endoscope shown in FIG. 32.

A stapler/endoscope 165 according to an eleventh embodiment of the invention will be described, with reference to FIGS. 32 to 34. The stapler/endoscope 165 is essentially the same as the tenth embodiment shown in FIG. 30, and its components identical to those of the tenth embodiment will be denoted by the same numerals and will now be described in detail.

Figure 32:
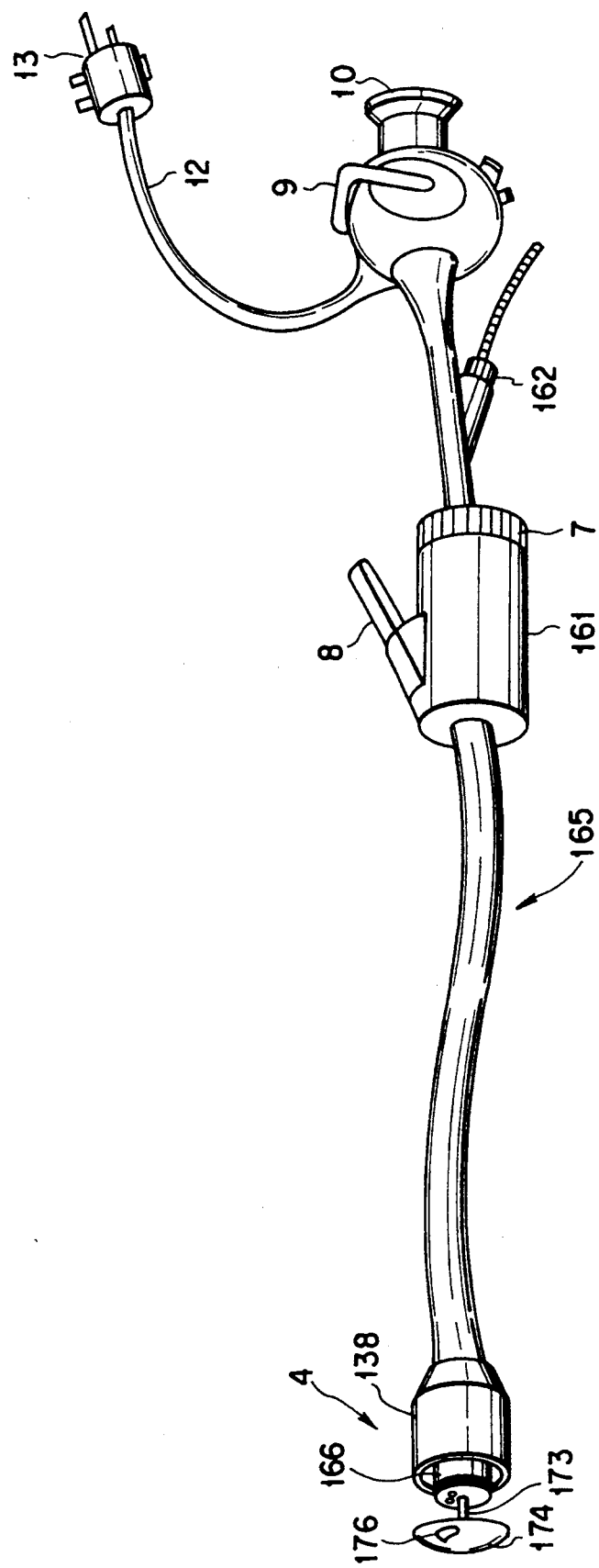
FIG. 32 is a perspective view of a stapler/endoscope according to an eleventh embodiment of the present invention.

The housing 138 contains a suction member 166 which can be moved back and forth by rotating the anvil-rotating knob 7 mounted on an operation section 161 as shown in FIG. 32. The suction member 166 has an observation system 167 and illumination systems 168 as is shown in FIG. 33. An annular suction groove 169 is formed in the circumference of the distal end portion of the suction member 166. As shown in FIG. 34, a suction port 170 is made in the distal end portion of the suction member 166, opening at the bottom of the suction groove 169. The suction groove 169 communicates via the suction port 170 with a suction tube 171 which extends through the suction member 166.

A guide pipe 172 extends through the suction member 166 along the axis thereof. An anvil shaft 173 is slidably inserted in the guide pipe 172. Secured to the distal end of the anvil shaft 173 is an anvil 174 which is a disk having a rounded front and a flat back. The proximal end of the anvil shaft 173 is connected to an anvil-operating knob 162 (FIG. 32) coupled to the operation section 161. The anvil 174 has an opening 176 which is aligned with the observation system 167 and the illumination systems 168.

How the stapler/endoscope 165 is operated will be described with reference to FIG. 35.

Figure 35:
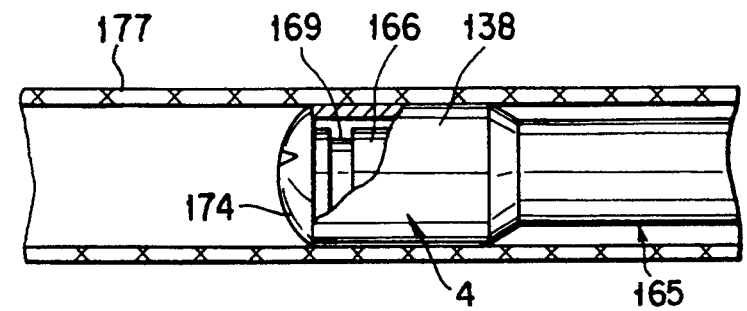
FIGS. 35(a)-35(e) show diagrams explaining how the stapler/endoscope of FIG. 32 is operated.
Figure 35:
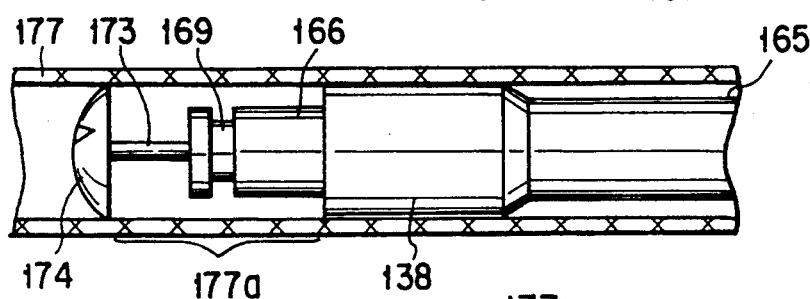
Figure 35:
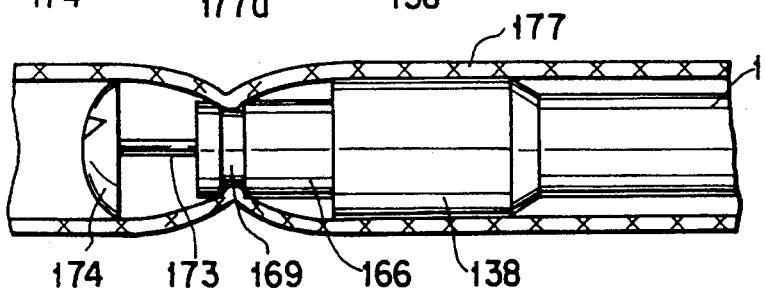
Figure 35:
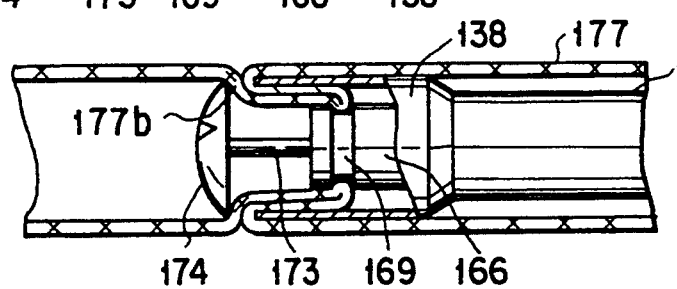
Figure 35:
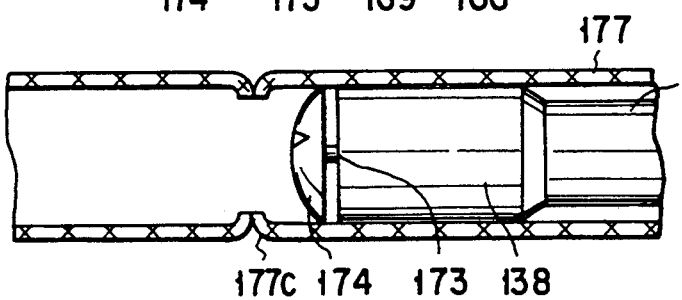

First, the anvil shaft 173 is pulled back into the guide pipe 138, moving the anvil 174 backward until it abuts on the housing 138 as is shown step (a) in FIG. 35. Then, the distal end portion 4 of the stapler/endoscope 165 is inserted into the intestine 177 through the anus and guided to a diseased portion 177a of the intestine 177.

Next, the anvil-operating knob 162 is rotated, thrusting the anvil shaft 173 forward, such that the gap between the housing 138 and the anvil 174 extends over the diseased portion 177a of the intestine 177 as is illustrated step (b) in FIG. 35. The space defined by the housing 138, the anvil 174 and the diseased portion 177a is evacuated through the suction groove 169 and the suction tube 171. The pressure in that space is thereby made lower than the pressure outside the intestine 177. As a result, the diseased portion 177a collapses, with its middle portion drawn into the suction groove 169, as is illustrated step (c) in FIG. 35.

In this condition, the suction member 168 is pulled back, moving the anvil 174 toward the housing 138. The diseased portion 177a of the intestine 177 is thereby drawn into the housing 138, folded double, as is shown step (d) in FIG. 35. The folded portions 177b of the intestine 177 are clamped between the housing 138 and the anvil 174.

Then, the staples 125 are driven into the folded portions 177b of the intestine 177, in the same manner as in the embodiments described above. The legs of each staple 125 pierce the walls 113 and 114, abut on the bottom of the groove 148 formed in the back of the anvil 146, are bent toward each other, thus stapling the folded portions 177b. Simultaneously, the annular cutter is thrust forward, excising those parts of the folded portions 177b which should be removed, as is illustrated step (e) in FIG. 35.

Another stapler/endoscope, which is a twelfth embodiment of this invention, will be described with reference to FIG. 36. This embodiment is basically identical to the eleventh embodiment shown in 32, 33, and 34. The components identical to those of the eleventh embodiment will be denoted by the same numerals and will now be described in detail.

Figure 36:
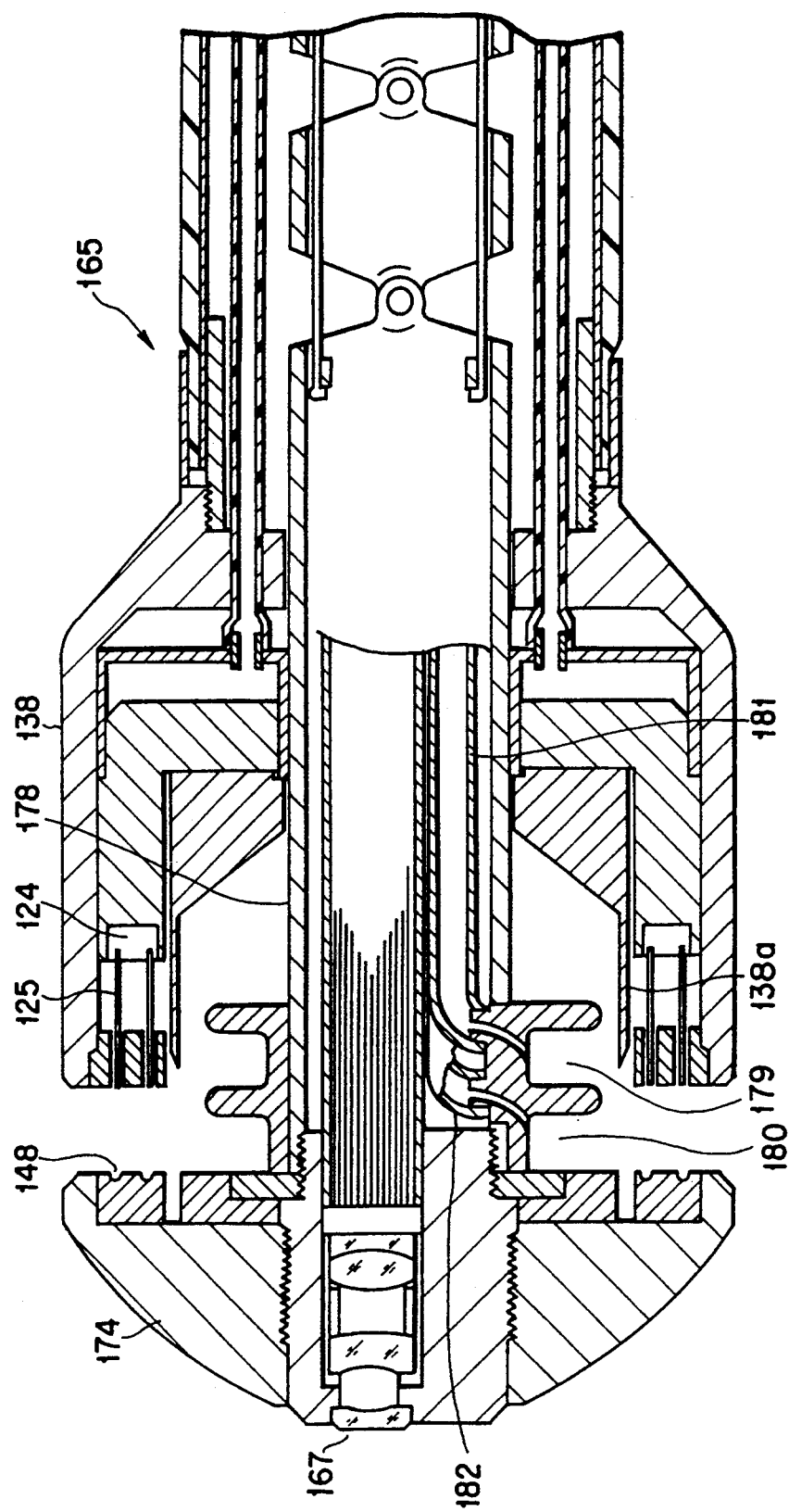
FIG. 36 is a sectional side view showing the distal end portion of a stapler/endoscope according to a twelfth embodiment of the present invention.

As shown in FIG. 36, a ring having two suction grooves 179 and 180 is mounted on the distal end of a suction member 178. The suction grooves 179 and 180 communicate with first and second suction tubes 181 and 182, respectively, which extend through the suction member 178.

How to operate the stapler/endoscope will be described with reference to FIG. 37. First, a diseased portion 177d of the intestine 177 is excised by forming an opening in the abdominal wall or by using a laparoscope. The suction member 178 is pulled into the housing 138, thus moving the anvil 138 into contact with the housing 138. Then, the distal end portion 4 of the stapler/endoscope is inserted into the intestine 177 through the anus and guided to one of the severed edges 177e of the intestine 177, as is illustrated step (a) in FIG. 37.

Next, the anvil-operating knob (not shown) is rotated, thrusting the anvil 174 forward from the housing 138, projecting the anvil 174 from the severed edge 177e of the intestine 177, as is illustrated step (b) in FIG. 37. The space defined by the housing 138, the anvil 174 and the severed edge portion 177e is evacuated through the first suction tube 181. As a result, the severed edge portion 177e is drawn into the first suction groove 179, as is illustrated in step (b) in FIG. 37.

Thereafter, the distal end portion 4 is further thrust forward, inserting the anvil 174 into the other severed edge portion 177f. The space defined by the anvil 174, the second suction groove 180, and the severed edge portion 177f is evacuated through the second tube 182. As a result, the severed edge portion 177f is drawn into the second suction groove 180, as is illustrated in step (c) in FIG. 37.

Next, the suction member 178 is pulled back, moving the anvil 174 back toward the housing 138. The severed edge portions 177d and 117f of the intestine 177 are thereby clamped between the housing 138 and the anvil 174 as shown in step (d) in FIG. 37. The staples 125 are driven from the housing 138 into the edge portions 177e and 117f thus clamped. The legs of each staple 125 pierce the severed edge portions 177e and 177f, abut on the bottom of the groove 148 formed in the back of the anvil 146, are bent toward each other, thus stapling the edge portions 177e and 177f. Simultaneously, the annular cutter 138a (FIG. 36) is thrust forward, excising those parts 177c of the stapled portions 177e and 177f which should be removed, as is illustrated in step (e) in FIG. 37.

Then, the distal end portion 4 is pulled back from the stapled portions 177e and 177f of the intestine 177 as is shown in step (e) in FIG. 37. At this time, the stapled portions 177c are examined by using the observation system 167 (FIG. 36). Thereafter, the distal end portion 4 is pulled out of the intestine 177 through the anus.

A stapler/endoscope according to a thirteenth embodiment of this invention will be described with reference to FIGS. 38 to 42.

Figure 38:
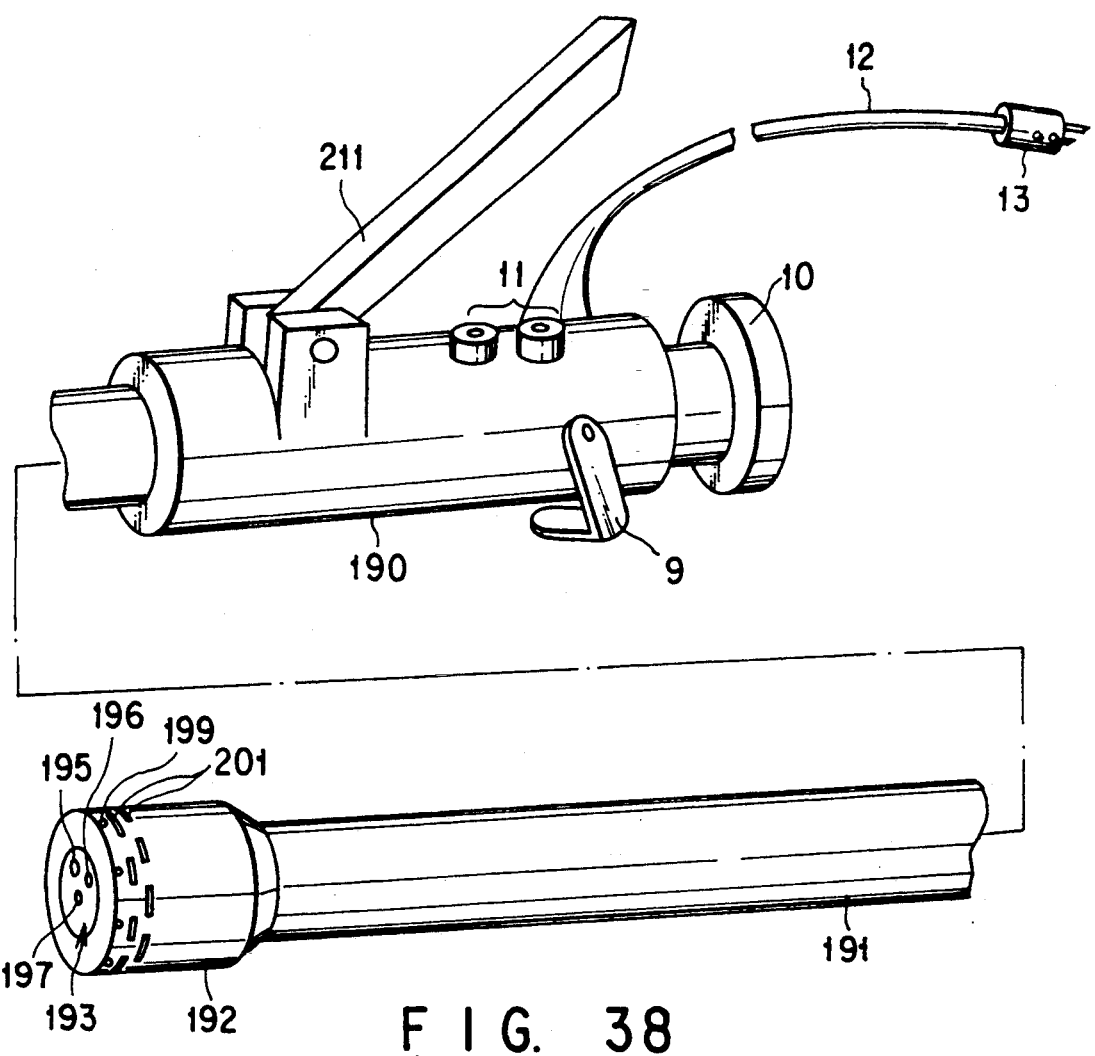
FIG. 38 is a perspective view of a stapler/endoscope according to a thirteenth embodiment of the present invention.

As FIG. 38 shows, this device comprises an operation section 190, an insertion section 191 connected to the distal end of the operation section 190, a housing 192 coupled to the distal end of the insertion section 191, and an endoscope 193 having a flexible tube 194 extending through the operation section 190 and the insertion section 191. The flexible tube 194 contains an observation system 195, illumination systems 196, an air/water supplying channel 197, and a suction tube 198.

Figure 39:
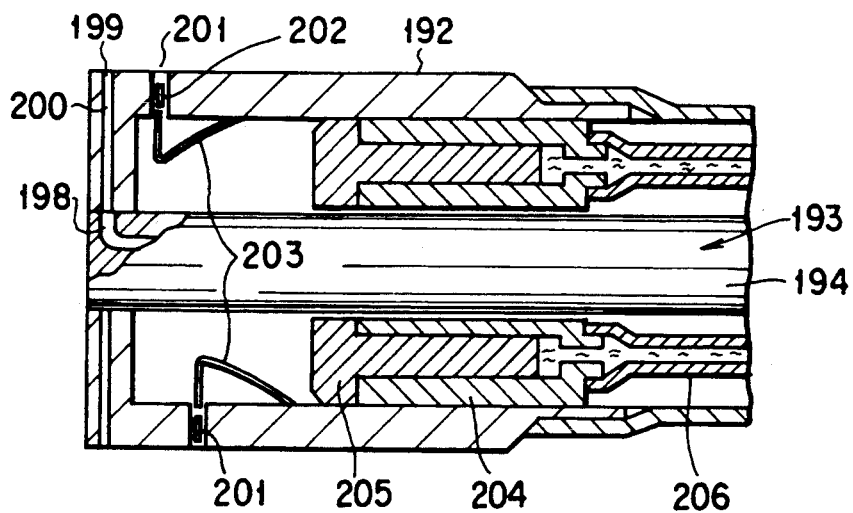
FIG. 39 is a sectional side view showing the staple-applying section of the stapler/endoscope shown in FIG. 38.

The housing 192 has suction holes 199 formed in its distal circumference and arranged equidistantly along its circumference. As shown in FIG. 39, the suction holes 199 are connected by suction ports 200 to the suction tube 198 which extends through the flexible tube 194.

Figure 40:
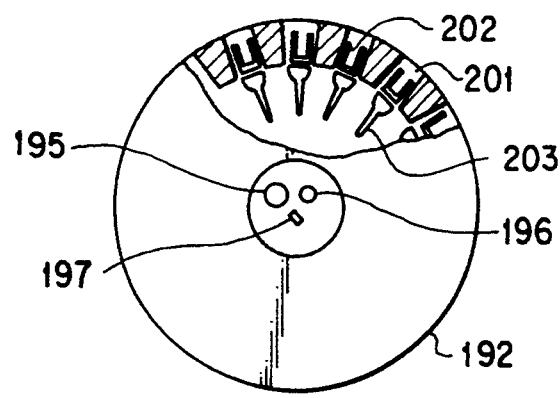
FIG. 40 is a cutaway front view showing the housing of the stapler/endoscope shown in FIG. 38.

As can be understood from FIGS. 38, 39, and 40, the housing 192 has slits 201 formed in its distal circumference, arranged in two rows, and spaced apart equidistantly along the circumference. As shown in FIGS. 39 and 40, staples 202 are loosely inserted in the slits 201. L-shaped staple pushers 203 are arranged in the housing 192. The staple pushers 203 are secured at one end to the inner surface of the housing 192. The other end of each staple pusher 203 is inserted in the corresponding slit 201.

In the housing 192, an annular cylinder 204 is located at the back of the staple pushers 203. A pusher ring 205 is slidably fitted in the annular cylinder 204. When hydraulic power is applied to the annular cylinder 204, the pusher ring 205 will be moved forward from the cylinder 204 and abut on the staple pushers 203, thrusting the free ends of the pushers 203 into the slits 201. As a result, the staples 202 are ejected outwards from the slits 201.

Figure 41:
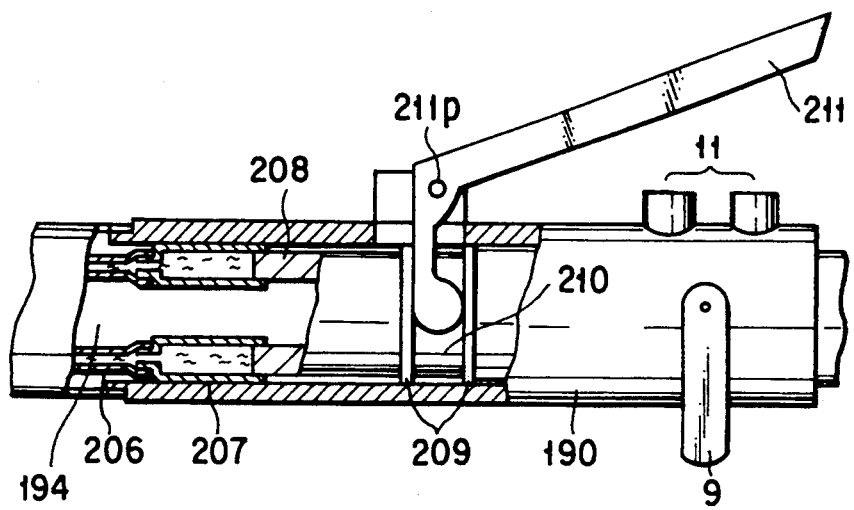
FIG. 41 is a cutaway side view of the operation section of the stapler/endoscope shown in FIG. 38.

The annular cylinder 204 is connected to the distal end of hydraulic tubes 206 which extend through the insertion section 191. As shown in FIG. 41, the hydraulic tubes 206 are connected at their proximal end to a hydraulic cylinder 207 located in the operation section 190. The hydraulic cylinder 207 is filled with oil, and a pressure ring 208 is slidably inserted in the proximal portion of the cylinder 207.

A pair of flanges 209 are secured to the proximal end portion of the pressure ring 208, defining a groove 210 between them. An L-shaped handle 211 is connected to the operation section 190 by a pin 211p, with its short arm engaged in the groove 210. When the handle 211 is squeezed, the pressure ring 208 will be pushed forward, applying the hydraulic power via the hydraulic tubes 206 to the pusher ring 205.

Figure 42:
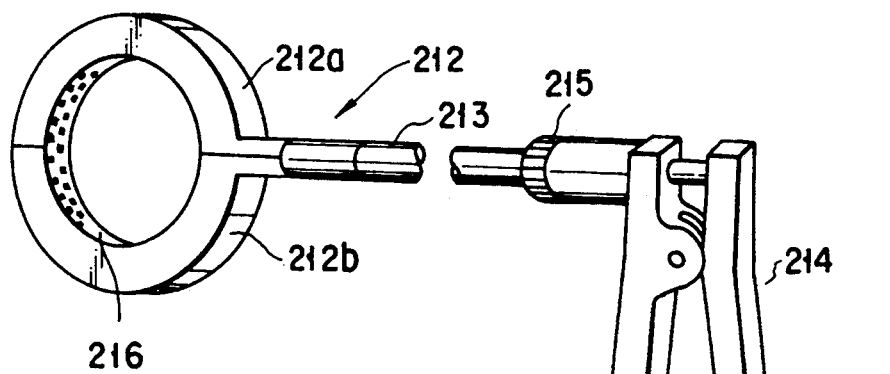
FIG. 42 is a perspective view illustrating the anvil forceps of the stapler/endoscope shown in FIG. 38.

The stapler/endoscope according to the thirteenth embodiment of this invention further comprises an anvil forceps 212 shown in FIG. 42. The anvil forceps 212 comprises two arcuate anvil halves 212a and 212b, an insertion section 213, a pair of handles 214, and a ring 215. Both anvil halves 212a and 212b are coupled to the distal end of the insertion section 213, and can rotated to move between their open and closed positions. The first handle 214 is fixed to the proximal end of the insertion section 213, and the second handle 214 is rotatably coupled to the first handle 214. When the second handle 214 is rotated, the anvil halves 212a and 212b will be moved to their open position or their closed position. The ring 215 is rotatably mounted on the insertion section 213. When the ring 215 is rotated, the insertion section 213 will be rotated around its axis.

Each anvil half has a plurality of grooves 216 formed in its inner circumference and arranged in two rows. These grooves 216 will oppose the staples 202 inserted in the slits 201 of the housing 192 when the anvil halves 212a and 212b are mounted on the distal end portion of the housing 192.

The operation of the stapler/endoscope shown in FIGS. 38 to 42 will be explained with reference to FIGS. 43A and 43B. First, a diseased portion 177d of the intestine 177 is cut and removed by forming an opening in the abdominal wall or by using a laparoscope. The distal end portion of the stapler/endoscope is inserted into the intestine 177 through the anus, guiding the housing 192 to the severed edge portion 177d of the intestine 177 as is shown in step (a) in FIG. 43.

Next, air is drawn into the suction holes 199 formed in the outer circumference of the housing 192, whereby the severed edge portion 117d is attracted onto the circumference of the housing 192. Then, the housing 192 is thrust forward into the other severed edge portion of the intestine 177 as is illustrated step (b) in FIG. 43.

The anvil halves 212a and 212b are mounted on the distal end portion of the housing 192 and so positioned that the grooves 216 oppose the staples 202 inserted in the slits 201 of the housing 192. This done, the second handle 214 of the anvil forceps is squeezed, whereby the overlapping portions of the intestine 177 are clamped between the anvil halves 212a and 212b, on the one hand, and the outer circumference of the housing 192, on the other.

Then, the handle 211 is squeezed, pushing the pressure ring 208 forward and applying the hydraulic power via the hydraulic tubes 206 to the pusher ring 205. As a result, the staples 202 are driven from the slits 210 into the overlapping portions of the intestine 177.

Figure 44:
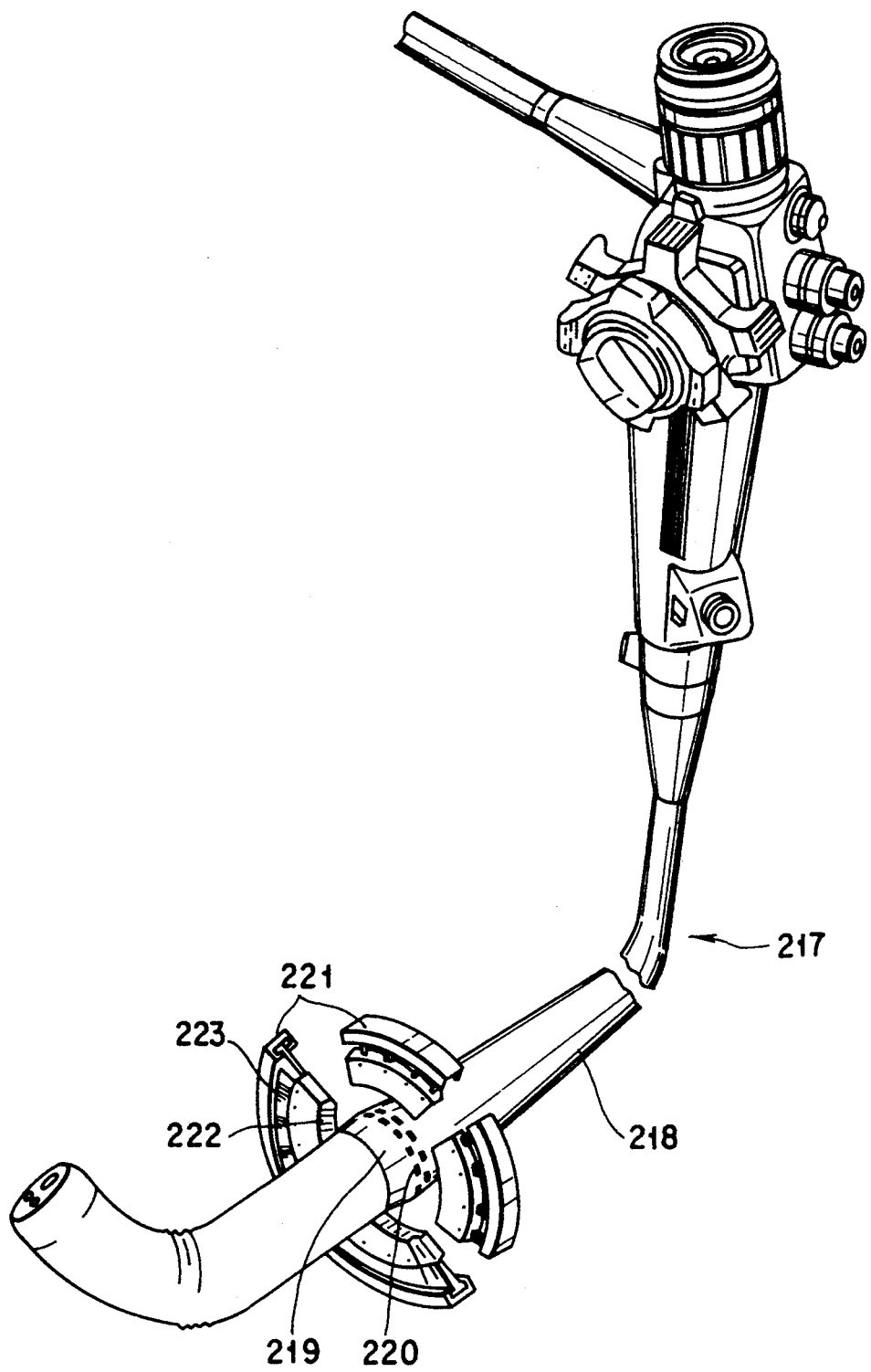
FIG. 44 is a perspective view of a stapler/endoscope which is a fourteenth embodiment of the present invention.
Figure 60A:
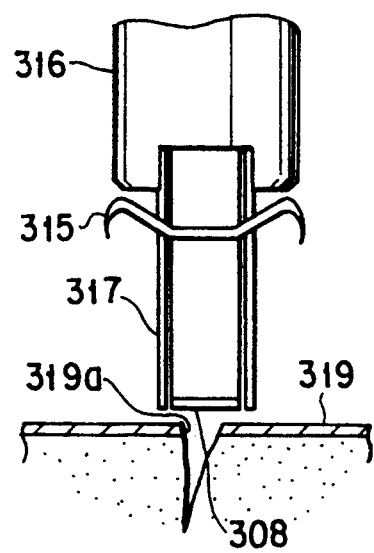
FIGS. 60(a)–60(d) show diagram explaining how the stapler/endoscope shown in FIG. 59A is operated.
Figure 60B:
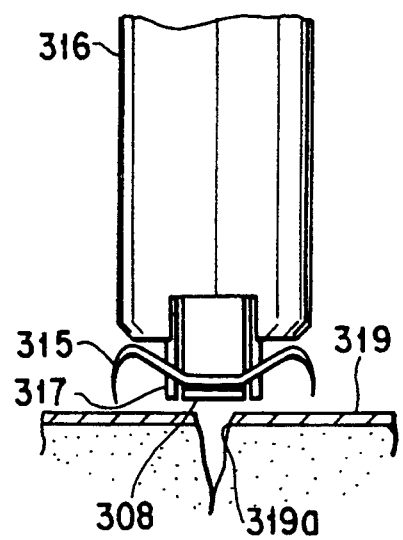
Figure 60C:
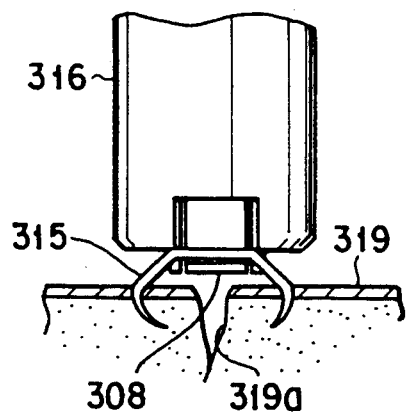
Figure 60D:
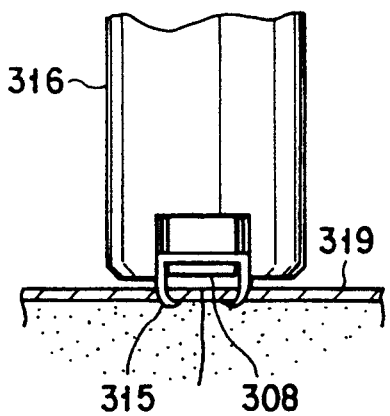
Figure 61:
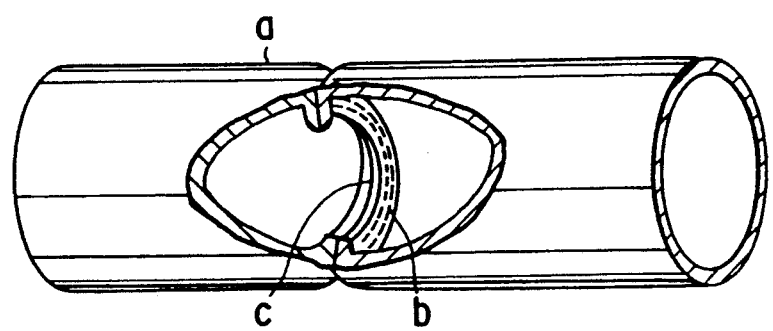
FIG. 61 is a cutaway perspective view of showing two portions of the intestine, which have been stapled together by means of the stapler/endoscope.

Another stapler/endoscope 217, which is a fourteenth embodiment of the invention, will be described with reference to FIG. 44. In the device 217, an anvil 219 is mounted on the middle portion of the insertion section 218. The anvil 219 has grooves 220 formed in its outer circumference. An annular cartridge 221 is mounted on the anvil 219. The cartridge 221 comprises a plurality of arcuate segments. A staple-driving mechanism 223 is arranged in the inner circumference of the cartridge 221, for driving staples 222.

The stapler/endoscope 217 is used in the following way. First, the distal end portion of the stapler/endoscope 217 is inserted into the intestine, guiding the anvil 219 to that portion of the intestine which is to be stapled. Then, the cartridge 221 is mounted on said portion of the intestine. The wall of that portion of the intestine is thereby clamped between the anvil 219 and the cartridge 221. Next, the staple-driving mechanism 223 is actuated, driving the staples 222 into the intestine wall. The legs of each staple 222 pierce the intestine wall, abut on the bottom of the grooves 220 formed in the circumference of the anvil 219, are bent toward each other, thus stapling the intestine wall.

A stapler according to a fifteenth embodiment of the invention will be described with reference to FIG. 45. As can be understood from FIG. 45, this stapler is similar to the first embodiment shown in FIGS. 1 and 2 but characterized in that a radial ultrasonic probe 224 is mounted on the outer circumference of the housing 30 of the stapling member 4. After target tissues are clamped between the anvil 6 and the housing 30, the radial ultrasonic probe applies ultrasonic waves to the clamped tissues, thereby determining whether or not blood vessels run through the clamped tissues. If the tissues are found to contain blood vessels, other parts of the tissues, which contains no blood vessels, will be clamped and stapled together.

A stapler according to a sixteenth embodiment of the invention will be described with reference to FIG. 46. This stapler is identical to the fifth embodiment (FIGS. 12 and 13), except that the anvil 84 has two linear ultrasonic probes 225a and 225b on the flat surface. More precisely, the first probe 225a extends beside the two rows of grooves 87, and the second probe 225b is located on the distal end portion of the anvil 84. The first probe 225a has a top sloping down toward the cutter-guiding groove 227 formed in the flat surface of the anvil 84 and extending along the axis thereof. The second probe 225b has a top sloping down toward the proximal end of the anvil 84.

The probes 225a and 225b apply ultrasonic waves to the tissues clamped between the anvil 84 and the cartridge (not shown), receive the ultrasonic waves reflected from the tissues, and generate echo signals. The echo signals are processed by a processing device (not shown), thereby to determine whether or not the tissues contain blood vessels and to calculate the rate at which the blood flows in the tissues. The stapler has a safety mechanism which automatically disables the stapling member (not shown) when the blood flow rate calculated is higher than a predetermined value.

If the tissues clamped between the anvil 84 and the cartridge contain blood vessels, the safety mechanism functions, whereby staples are not driven into the tissues. If the tissues contain no blood vessels, the safety mechanism does not work, whereby staples are driven into the tissues. Hence, the stapler according to the sixteenth embodiment enables a surgeon to staple target tissues together neatly and properly even if he or she is not so skilled.

Another stapler according to a seventeenth embodiment of this invention will be described with reference to FIGS. 47 to 49. As can be understood from these figures, a Doppler transducer 229 and a pair of jaws 230 are coupled to the distal end of the insertion section 228. The stapler is designed to apply a hemostatic clip or staple 231 to a tubular organ such as a blood vessel. More specifically, the clip 231 is held between the jaws 230 and will be plastically deformed to clamp a blood vessel between it legs. The jaws 230 and the clip 231 are so located to receive and reflect ultrasonic waves applied from the transducer 229. Therefore, their presence or absence can be detected from the echo signals generated by the transducer 229.

The transducer 229 may be separated into two parts 229a and 229b, which are located above and below the jaws 230, respectively, as is illustrated in FIG. 50. In this case, the first transducer 229a applies ultra sonic waves to a tubular organ, and the second transducer 229b receives the ultrasonic waves reflected from the organ. A balloon may be connected to the distal end of the insertion section 228, and water may be introduced into the balloon.

Assume the organ bleeds much, forming a pool of blood, and the position of the bleeding is not known. The distal end of the insertion section 228 is immersed in the pool of blood, and the transducer 229 applies ultrasonic waves to the organ. The jaws 230 holding the clip 231 are thereby guided to the position of bleeding and operated to clamp the bleeding portion of the organ with the clip 231, thereby stopping the bleeding. If the pool of blood is small, the balloon may be filled with water, and then the transducer 229 may apply ultrasonic waves to the organ.

A stapler according to an eighteenth embodiment of the invention will be described with reference to FIGS. 51 and 52.

As shown in FIG. 52, a wire guide 233 is coupled to the distal end of the insertion section 232. A guide wire 234 extends from the operation section (not shown) through the insertion section 232 and the wire guide 233; it can be pulled back and forth. The guide wire 234 is removably connected to the wire connector 236 which is secured to an anvil 235.

The stapler shown in FIGS. 51 and 52 is manipulated in the following way to stitch the small intestine 238 to the stomach 237 and to form a passage between these organs. First, the anvil 235 is inserted into a severed end portion of the small intestine 238 by using a laparoscope or through an opening surgically formed in the abdominal wall. Then, the severed end of the small intestine 238 is tied up with a thread 239 around the connector 236. Also, an opening 241 is formed in the wall 240 of the stomach 237.

Then, as shown in FIG. 51, an endoscope 242 is inserted into the stomach 237 through the mouth. The guide wire 234 is fed forward through the opening 241 into the connector 236. Next, the endoscope 242 is pulled from the stomach 237. The insertion section 232 of the stapler is inserted into the stomach 237, using the guide wire 234, as is shown in FIG. 52. The guide wire 234 is pulled into the insertion section 232, thereby moving the severed end of the small intestine 238 into contact with the wall 240 of the stomach 237. The wall 240 and the severed edge of the small intestine 238 are thereby clamped between the anvil 235 and the distal end of the insertion section 232. In this condition, staples (not shown) are driven into the wall 240 and the severed edge of the small intestine 238, stitching the small intestine 238 to the stomach 237 as is shown in FIG. 53.

Another stapler/endoscope 251, which is a nineteenth embodiment of the present invention, will be described with reference to FIGS. 54 to 56.

As shown in FIG. 54, the stapler/endoscope 251 comprises a grip 252 and an insertion section 253 coupled to the grip 252. Jaws 254 are connected to the distal end of the insertion section 253. As shown in FIG.

55, the jaws 254 are a cartridge 255 and an anvil 256. The cartridge 255 has a plurality of staples. The anvil 256 is rotatably connected to the distal end of the insertion section 253 and can assume an open position and a closed position with respect to the cartridge 255.

As is shown in FIG. 56, the distal end of the anvil 256 contains an observation system 257 and two illumination systems 258 and 259. The observation system 257, which comprises an objective 260 and a light-guiding fiber 261, is located between the illumination systems 258 and 259. The cartridge 255 has a knife 262 protruding from the inner surface which opposes the anvil 256. The knife 262 can be moved back and forth along a guide groove formed in the inner surface of the cartridge 255 and extending straight along the axis thereof. The anvil 256 also has a guide groove 263 for guiding the knife 262.

Referring back to FIG. 54, an anvil-operating knob 264 is mounted on the distal end portion of the grip 252, and a lever 265 is rotatably coupled to the grip 252. When rotated, the knob 264 opens and closes the anvil 256 with respect to the cartridge 255. When squeezed, the lever 265 drives the staples from the cartridge 255 and thrusts the knife 262 forward.

The grip 252 is connected by a universal cord 266 to a light source 267 and a camera control unit 268. A monitor 269 is connected to the camera control unit 268. Hence, light can be applied from the light source 267 to both illumination systems 258 and 259, and the camera control unit 268 can receive the image transmitted from the observation system 257 and convert it into image signals, which are supplied to the monitor 269. The monitor 269 can therefore display, on its screen, an image identical to the image transmitted from the observation system 257.

The stapler/endoscope 251 is operated in the following manner. First, a surgeon inserts the insertion section 253 into a body cavity through a trocar 270. Seeing the image of the body cavity transmitted from the observation system 257 and displayed by the monitor 269, the surgeon moves the stapler/endoscope 251, guiding the jaws 254 to target tissues within the body cavity.

Next, the surgeon rotates the anvil-operating knob 264, thereby opening the anvil 256. When the target tissues are caught between the cartridge 255 and the anvil 256, the surgeon rotates the knob 264 in the opposite direction, thereby closing the anvil 256 and subsequently clamping the tissues between the cartridge 255 and the anvil 256. He or she then squeezes the lever 265, whereby the staples are driven from the cartridge 255 into the tissues, fastening the tissues together.

Thereafter, the surgeon rotates the knob 264, opening the anvil 256, so that the observation system 257 transmits the image of the stapled tissues to the camera control unit 268. Seeing the image displayed by the monitor 269, the surgeon determines whether the tissues have been properly stapled or not. If he or she finds the tissues appropriately stapled, he or she pulls the insertion section 253 for some distance, thus releasing the tissues from the jaws 254.

Since the observation system 257 is located at the tip of the anvil 256, it can easily catch sight of the target tissues. This helps the surgeon to guide the insertion section 253 to the target tissues which are likely to remain unseen through an ordinary endoscope.

Further, since the tissues are not hooked at the tips of the jaws 254, they can be reliably caught between the jaws 254. In addition, it is possible to determine whether or not each staple has been appropriately driven into the tissues.

The observation system 257 is an optical system having a glass fiber. This system may be replaced by an imaging device such as a CCD. Further, the observation system 257 may be removed, leaving a channel in the anvil 256, and a fiber scope or an ultrasonic probe may be inserted into the body cavity through that channel.

A stapler/endoscope according to a twentieth embodiment of this invention will be described with reference to FIG. 57. This device is identical to the nineteenth embodiment, except that a bending portion 271 is connected to the distal end of the insertion section 253 and that the jaws 254 are connected to the distal end of the bending portion 271. The bending portion 271 can be bent by rotating a lever coupled to the grip 252, thereby directing the jaws 254 upward or downward and leftward or rightward.

More specifically, the bending portion 271 comprises a plurality of segments 272, a pair of operating wires 273, and another pair of operating wires 274. The segments 272 are connected such that they constitute a flexible unit that can be bent upward, downward, leftward, and rightward. When one of the operating wires 273 is pulled, while the other is slackened, the flexible unit is bent upward or downward. When one of the operating wires 274 is pulled, while the other is slackened, the flexible unit is bent leftward or rightward.

Since the jaws 254 are coupled to the bending portion, they can be directed upward, downward, leftward, and rightward, by operating the lever coupled to the grip 252. Therefore, the jaws can catch the target tissues between them, more easily and more reliably than otherwise. Provided at the tip of the anvil 256, the observation system 257 can take various positions with respect to the target tissues. This enables a surgeon to see the target tissues from different angles and, hence, to examine the tissues more accurately.

A clip applicator/endoscope 281 according to a twenty-first embodiment of this invention will be described with reference to FIGS. 58A to 58C.

As shown in FIG. 58A, this device 281 comprises a grip 282 and an insertion section 283 coupled to the grip 282. A lever 284 is slidably mounted on the grip 282, and a handle 285 is rotatably connected to the grip 282. A bending portion 286 is connected to the distal end of the insertion section 283. The portion 286 can be bend by operating the lever 284. Connected to the bending portion 286 is a distal end portion 287. Jaws 288 are connected to the distal end portion 287, for holding a clip between them. An observation means 289 is mounted on the bending portion 286 and located at the proximal ends of the jaws 288.

As FIG. 58B shows, the observation means 289 has an observation system 290 and two illumination systems 291 positioned on the sides of the observation system 290. As can be understood from FIG. 58C, the observation system 290 comprises an objective 292 and a light-guiding fiber 293. As shown in FIG. 58C, the distal end portion 287 contains a plurality of clips 294 and a clip feeder 295 for feeding the clips 294, one by one.

Referring back to FIG. 58A, the grip 282 is connected by a universal cord 296 to a light source 267 and a camera control unit 268. A monitor 269 is connected to the camera control unit 268. Hence, light can be applied from the light source 267 to both illumination systems 291, and the camera control unit 268 can receive the image transmitted from the observation system 290 and convert it into image signals, which are supplied to the monitor 269. The monitor 269 can therefore display, on its screen, an image identical to the image transmitted from the observation system 290.

While seeing the images 288' of the jaws 288 and target tissues on the screen of the monitor 269, a surgeon can guide the jaws 288 to target tissues which are to be clipped. When the target tissues are caught between the jaws 288, the surgeon closes the jaws 288, clamping the tissues and applying a clip 294 to the tissues.

Located at the proximal ends of the jaws 288, the observation means 287 has its view field never blocked by the insertion section 283. Hence, the monitor 269 displays the jaws 288 and the tissues at all times during the operation. The surgeon can therefore guide the jaws 288 to the target tissues more accurately than otherwise. Also, he or she can detect an abnormality, if any, at once, such as displacement of the clip 294 or bleeding in the target tissues.

The observation system 290 can be replaced by a solid-state imaging device, a laser Doppler device, or an ultrasonic probe.

A stapler/endoscope 301 according to a twenty-second embodiment of this invention will be described with reference to FIGS. 59A to 59C. The device 301 is designed to apply a V-shaped staple to a body tissue and bend the same to close a wound in the tissue.

As FIG. 59A shows, the stapler/endoscope 301 comprises a grip 302 and an insertion section 303 coupled to the insertion section 302. A lever 304 is slidably mounted on the grip 302, and a handle 305 is rotatably connected to the grip 302. A bending portion 306 is connected to the distal end of the insertion section 303. The portion 306 can be bend by operating the lever 304. A distal end portion 307 is connected to the bending portion 306.

As shown in FIG. 59B, an anvil 308 is secured to the tip of the distal end portion 307. As can be understood from FIG. 59C, the distal end portion 307 contains a blade 316 and a staple receptacle 314. The blade 316 can slide back and forth. The receptacle 314 contains a plurality of staples 315. Provided within the receptacle 314 is a bias means which biases the staples 315 toward the distal end of the anvil 308. As shown in FIG. 59C, a spring 37 is provided in the anvil 308, for ejecting the staple 315.

The distal end portion 307 has an observation means 309 which is located near the anvil 308. The observation means 309 has an observation system 310 and an illumination system 311. The observation system 310 comprises an objective 312 and a light-guiding fiber 313. The illumination system 311 is a hollow cylindrical member surrounding the observation system 310.

The stapler/endoscope 301 is manipulated in the following way.

First, the surgeon guides the distal end portion 307 to a target tissue 319, while seeing on the screen of the monitor 269 the image of the body cavity containing the target tissue 319. Then, the distal end portion 307 is moved, placing the anvil 308 right above the wound 319a in the tissue 319, as is shown in step (a) in FIG. 60. The blade 314 is thrust forward, feeding a staple 315 until the staple 315 abuts on the anvil 308 as is illustrated step (b) in FIG. 60. At this time, the monitor 269 displays the image 308' of the anvil 308 and the image 315' of the staple 315, as shown in FIG. 59A.

The blade 316 is further thrust forward. Clamped between the anvil 308 and the blade 316, the staple 315 is gradually bent, with its legs driven into the tissue 319, as is shown step (c) in FIG. 60. As the blade 316 is thrust still further, the staple 315 is bent, having its legs connecting at the tip, as is illustrated step (d) in FIG. 60. As a result, the staple 315 gathers those portions of the tissue 319 which are located on the sides of the wound 319a, closing the wound 319a completely.

Located in the distal end portion 307 and near the anvil 308, the observation means 309 has its view field never blocked by the insertion section 303. Hence, the monitor 269 displays the image 308' of the anvil 308 and the image 315' of the staple 315 during the operation. The surgeon can therefore guide the anvil 308 to the wound 319a in the tissue 319 more accurately than otherwise. In addition, he or she can detect an abnormality, if any, at once, such as displacement of the staple 315 or bleeding in the target tissue 319.

The observation means 309 can be replaced by a solid-state imaging device, a laser Doppler device, or an ultrasonic probe.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A surgical device in combination with an endoscope, for stapling and fastening body tissues, said device comprising:
    holding means for holding a cassette containing a plurality of stapling/fastening members;
    applying means located in said holding means, for applying the stapling/fastening members to the body tissues;
    deforming means located in the vicinity of said holding means, for deforming the stapling/fastening members applied by said applying means, thereby fixing the stapling/fastening members to the body tissues;
    an insertion section having a proximal end portion and a distal end portion to which said holding means is connected, said insertion section being inserted into a channel of the endoscope; and
    an operation section removably connected to the proximal end portion of said insertion section after said insertion section is inserted into the channel of the endoscope, for operating said deforming means; an observation means located on a distal end of said endoscope;
    wherein said holding means is introduced into a body cavity by using the endoscope in order to staple the body tissues together.

2. The device according to claim 1, wherein said cassette is coaxial with said insertion section.

3. The device according to claim 1, wherein said insertion section is flexible.

4. The device according to claim 1, wherein said operation section is connected to said insertion section in the vicinity of an operation section of the endoscope.

5. The device according to claim 1, wherein said insertion section has a diameter of 3 mm or less.

6. The device according to claim 1, wherein said insertion section comprises:

a first component coupled to said holding means; and a second component coupled to said deforming means.

7. The device according to claim 1, wherein said holding means has at least one port through which to apply the stapling/fastening members in an axial direction of said insertion section, and said deforming means is movable in the axial direction of said insertion section and is moved with respect to said holding means when driven by operating said operation section.

* * * * *